(12) United States Patent
Cohen et al.

(10) Patent No.: US 7,771,427 B2
(45) Date of Patent: *Aug. 10, 2010

(54) PARTIALLY RESORBABLE CONNECTIVE TISSUE DISTRACTION DEVICES AND TECHNIQUES

(75) Inventors: Steven R. Cohen, La Jolla, CA (US); Ralph E. Holmes, San Diego, CA (US); J. Peter Amis, Carlsbad, CA (US); Horst R. Fichtner, Carlsbad, CA (US); Stefan M. Lemperle, La Jolla, CA (US)

(73) Assignee: Macropore, San Diego, CA (US)

( * ) Notice: Subject to any disclaimer, the term of this patent is extended or adjusted under 35 U.S.C. 154(b) by 2316 days.

This patent is subject to a terminal disclaimer.

(21) Appl. No.: 09/733,302

(22) Filed: Dec. 8, 2000

(65) Prior Publication Data

US 2002/0072747 A1 Jun. 13, 2002

Related U.S. Application Data

(60) Provisional application No. 60/170,011, filed on Dec. 9, 1999.

(51) Int. Cl.
*A61B 17/00* (2006.01)
*A61F 5/04* (2006.01)

(52) U.S. Cl. .................................................. 606/57

(58) Field of Classification Search ............. 606/53, 606/60, 151, 153, 154, 155, 69, 70, 71, 72, 606/73; 623/23.72, 23.75, 23.76

See application file for complete search history.

(56) References Cited

U.S. PATENT DOCUMENTS

| 3,604,414 A | 9/1971 | Borges |
| 4,119,092 A | 10/1978 | Gil |
| 5,084,051 A | 1/1992 | Törmälä et al. |
| 5,129,903 A | 7/1992 | Luhr et al. |
| 5,252,523 A | 10/1993 | Beall et al. |
| 5,281,226 A | 1/1994 | Davydov et al. |
| 5,290,281 A | 3/1994 | Tschakaloff |
| 5,364,396 A | 11/1994 | Robinson et al. |
| 5,672,177 A | 9/1997 | Seldin |
| 5,676,667 A | 10/1997 | Hausman |

(Continued)

FOREIGN PATENT DOCUMENTS

WO WO 97/27811 8/1997

(Continued)

OTHER PUBLICATIONS

Balch et al., Anthroscopy, 15:691-708 (1999).

(Continued)

*Primary Examiner*—Anu Ramana
(74) *Attorney, Agent, or Firm*—Shumaker & Sieffert, P.A.

(57) ABSTRACT

One aspect of the present invention is a connective tissue distraction device comprising: a first transmitting structure for transmitting force to a first tissue region and a second transmitting structure for transmitting force to a second tissue region by contact with bone, and an expansion device for exerting force distracting the first transmitting structure from the second transmitting structure. At least one of the first transmitting device, the second transmitting device and the expansion structure comprises in whole or in part a biodegradable, bioerodible or bioresorbable material.

26 Claims, 10 Drawing Sheets

U.S. PATENT DOCUMENTS

| | | | |
|---|---|---|---|
| 5,697,976 | A | 12/1997 | Chesterfield et al. |
| 5,766,710 | A | 6/1998 | Turnlund et al. |
| 5,769,850 | A | 6/1998 | Chin |
| 5,810,884 | A * | 9/1998 | Kim ............................ 606/213 |
| 5,866,155 | A | 2/1999 | Laurencin et al. |
| 5,876,452 | A | 3/1999 | Athanasiou et al. |
| 5,902,304 | A | 5/1999 | Walker et al. |
| 5,919,234 | A | 7/1999 | Lemperle et al. |
| 5,935,594 | A | 8/1999 | Ringeisen et al. |
| 5,981,619 | A | 11/1999 | Shikinami et al. |
| 5,997,568 | A | 12/1999 | Liu |
| 6,113,599 | A | 9/2000 | Landsberger |
| 6,280,473 | B1 * | 8/2001 | Lemperle et al. ......... 623/16.11 |
| 6,364,908 | B1 * | 4/2002 | Ysebaert .................. 623/15.12 |
| 6,371,985 | B1 * | 4/2002 | Goldberg ................. 623/16.11 |
| 6,423,069 | B1 * | 7/2002 | Sellers ......................... 606/71 |
| 6,548,569 | B1 * | 4/2003 | Williams et al. ............ 523/124 |

FOREIGN PATENT DOCUMENTS

| | | |
|---|---|---|
| WO | WO 98/07384 | 2/1998 |
| WO | WO 99/51171 | 10/1999 |
| WO | WO 01/41661 | 6/2001 |
| WO | WO 01/41662 | 6/2001 |

OTHER PUBLICATIONS

Chin and Toth, J. Oral Maxillofac. Surg., 54:45-53 (1996).
Cohen, Seminars in Orthodontics, 5:52-58 (1999).
Cohen et al., J. Craniofac. Surg., 10:244-251 (1999).
Constantino and Friedman, Otolaryngologic Clinis of N.A., 24:1433-1443 (1991).
Ilizarov, "The Principles of the Ilizarov Method" 48 Bull. of the Hospital for joint Diseases Orthopaedic Institute, 48:1-11 (1988).
Karp et al., Annals of Plastic Surgery, 24:231-237 (1990).
Karp et al., Annals of Plastic Surgery, 29:2-7 (1992).
Leibinger, Gen. Info. Modular Internal Distraction System, Scientific Documentation, Howmedica Leibinger Inc. (Jun. 3, 1998).
Leibinger, Modular Internal Distraction System, Scientific Documentation 90-02104, Howmedica Leibinger Inc. Carrollton, TX (Dec. 1998).
McGuire et al., Arthroscopy, 15:463-473 (1999).
Schliephake et al., J. Oral Maxillofac. Surg., 56:616-626 (1998).
Vert et al., J. Controlled Release, 53:85-92 (1998).

* cited by examiner

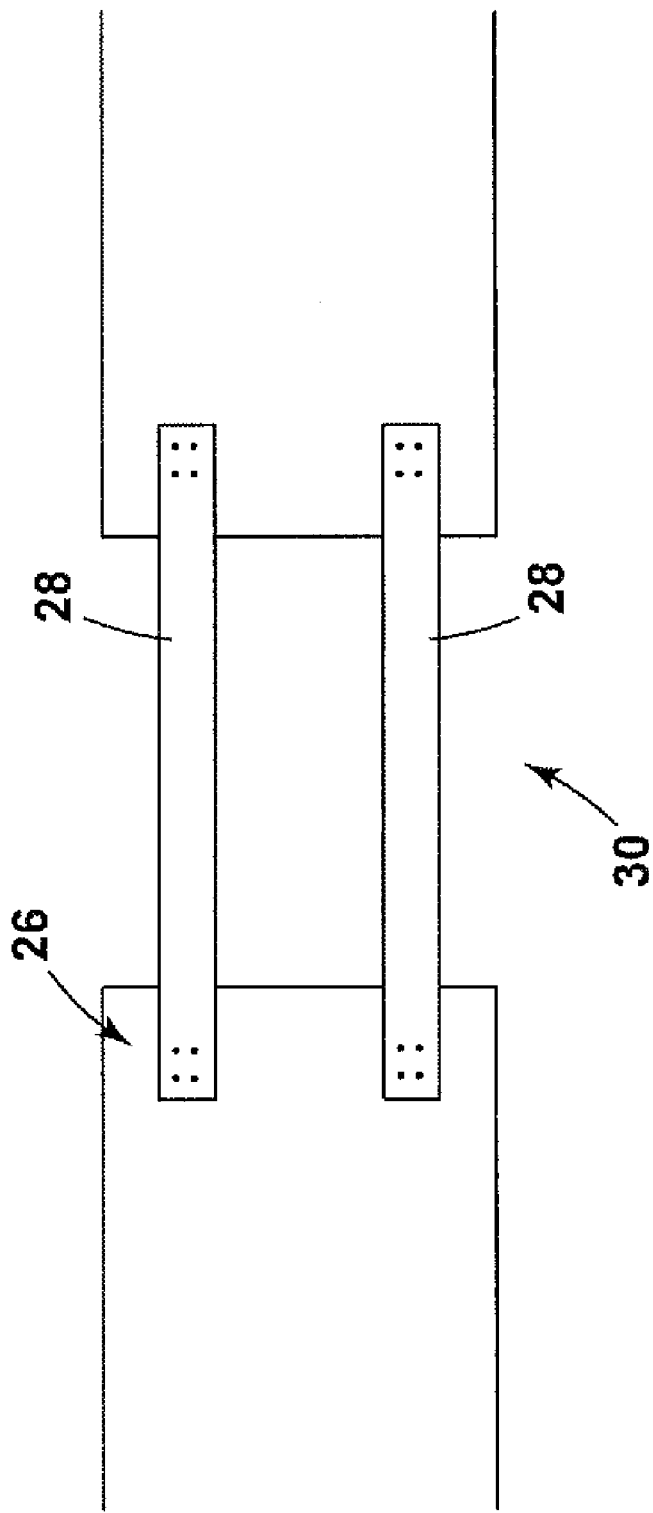

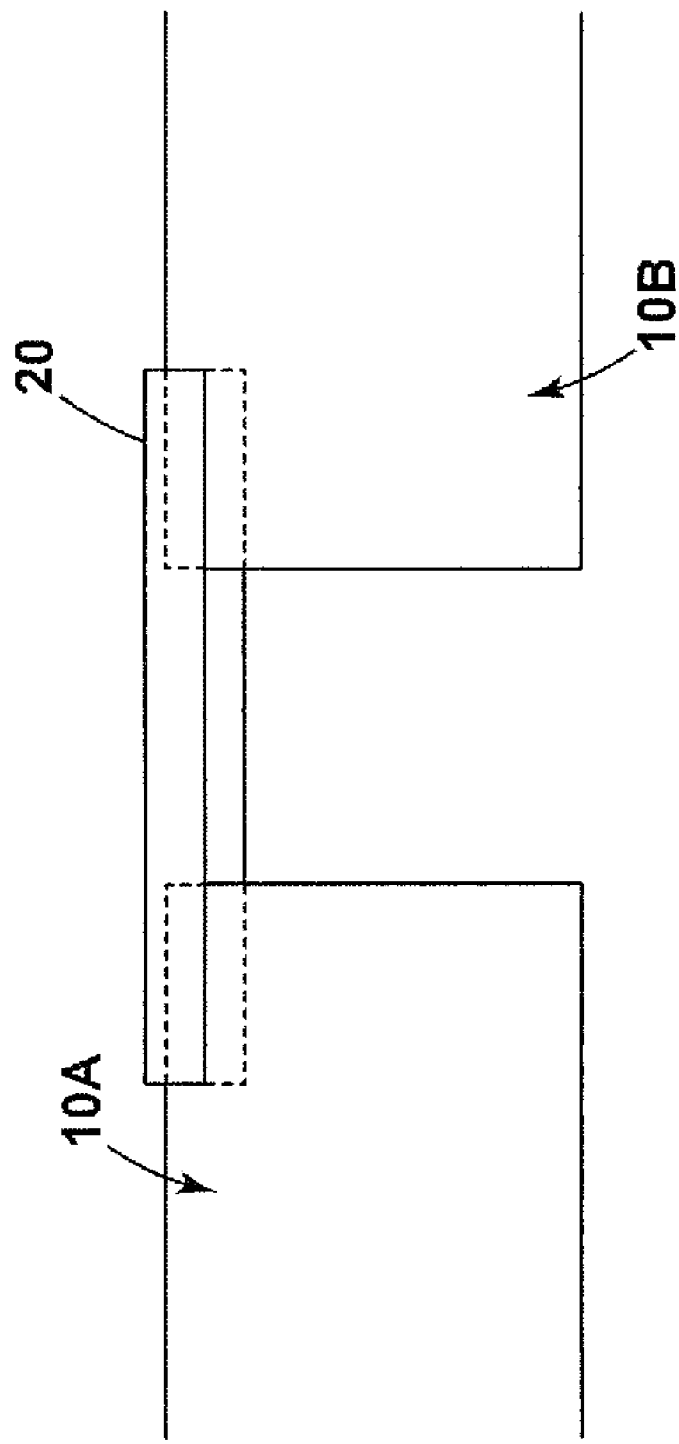

PARTIALLY RESORBABLE CONNECTIVE TISSUE DISTRACTION DEVICES AND TECHNIQUES

This application claims benefit of priority to U.S. provisional patent application No. 60/170,011, filed Dec. 9, 1999 to Cohen et al., which is incorporated by reference herein in its entirety.

TECHNICAL FIELD

The present invention generally related to devices and methods of distraction, particularly of connective tissue such as bone, such as in a human subject. Preferably, the devices and methods are used in human craniofacial bone distraction.

BACKGROUND OF THE INVENTION

Connective tissue is the tissue that binds together and supports the various structures of the body. It has been demonstrated that gradual application of force separating two or more portions of a canine or human connective tissue structure will result in deposition of extra cellular fibrous tissue components with permanent increase in tissue size and mass. E.g., Karp, N. S., McCarthy, J. G., Schneiber, J. S., Sissons, H. A., and Thorne, C. H. M., "Membranous Bone Lengthening: A Serial Histological Study," 29 Ann. Plast. Surg. 2-7 (1992); and Costantino, P. D. and Freidman, C. D., "Distraction Osteogenesis," 24 Otolaryngologic Clinics of N.A. 1433-43 (1991) ("Costantino et al."). In some instances this has been facilitated by cutting or breaking the tissue intermediate the tissue areas where force is applied by performing an osteotomy or corticotomy. In other instances, particularly involving growing tissue, such cutting or breaking is not necessary.

For instance, human bone lengthening by gradual distraction was demonstrated at least as early as 1905, but it has been more widely practiced only more recently, having been popularized by Ilizarov in Russia and De Bastiani and his associates in Italy. See McCarthy, J. G., Schneiber, J., Karp, N., Thorne, C. H., and Grayson, B. H., "Lengthening the Human Mandible by Gradual Distraction," 89 Plast. And Reconstruct. Surg. 1-8 (1992) ("McCarthy et al."); and Ilizarov, "The Principles of the Ilizarov Method," 48 Bull. of the Hospital for Joint Diseases Orthopaedic Institute 1-11 (1988). Gradual distraction offers distinct advantages as compared to bone grafting. Taylor, Discussion of McCarthy et al., 89 Plast. and Reconstruc. Surg. 9-10 (1992):

It provides new living bone of similar character, the soft tissues are lengthened without loss of sensation, there is no donor-site morbidity, and the technique may stimulate the efficiency of the reduced functional matrix in the region.

Id. At 10.

Most bone lengthening and corrective work has been done with respect to long bones in the arms and legs, although McCarthy, et al. have demonstrated that the mandible of human children can be lengthened by gradual distraction. See also Senezer, M., "Mandibular Lengthening by Gradual Distraction," 92 Plast. and Reconstruct. Surg. 372 (1993) (reporting lengthening of human adult mandibles).

Additionally, devices utilizing screw or other expansion mechanisms attached between and solely to the left and right maxillary teeth have been used in procedures that enlarge human palates. E.g., Epker, B., and Fish, L., 2 *Dental Facial Deformities* 818-875 (1986). At least some such procedures commence with substantial expansion of the maxilla during the initial surgical procedure. Id. At 831.

The mandibular distraction device utilized by McCarthy, et al., is a relatively large appliance mounted outside the patient's mouth on pins that pass through incisions in the cheek. Such distraction devices are heavy, unwieldy, unsightly and subject to damage or dislocation impact. Furthermore, such devices require incisions that leave scars that may be unsightly and require revision. As McCathy et al. have noted, better mandibular distraction devices are needed for these and other reasons. See also Costantino et al. at 1441; and Karp, N. S., Thorne, C. H. M., McCarthy, J. G., Sissons, H. A., "Bone Lengthening in the Craniofacial Skeleton," 24 Ann. Plast. Surg. 231, 236 (1990). Furthermore, gradual distraction of other craniofacial sites is desirable but generally has not been possible because of the limitations of existing devices.

Early midface distraction with buried devices were being performed in various centers by about 1993 (Cohen et al., J. Craniofac. Surg. 6:368 etc. (1995); Muhlbauer, Reconstructive and Aesthetic Surg. Meeting, Yokahoma, Japan, April 1995 (abstract)). Molina performed high Le Fort I osteotomoies and midface distraction by a reverse headgear that had the characteristics of a tooth-borne appliance (Molina, Workshop on Distraction of the Craniofacial Skeleton, New York University Medical Center, New York, N.Y., Mar. 18-19 (1994)). In addition, buried midface distraction was performed in a child with anophthalmia and left craniofacial micrisomia (Cohen et al., Craniofac. Sur. 6:368 etc. (1995)). In this instance, the outcomes were documented by cephalograms and coronal or three-dimensional computed tomographic scans. Muhlbauer conducted a series of Le Fort III and monobloc distraction in patients with Apert's syndrome (International Meeting of Plastic, Reconstructive, and Aesthetic Surgery in Yokohama, Japan (1995)). Chin and Toth reported buried distraction, including Le Fort III midfacial advancement (Chin and Toth, J. Oral Maxillofac. Surg. 54:45 etc. (1996)). Polley et al., using an external traction appliance, showed frontofacial advancement in a newborn with proptosis and upper airway obstruction (Polley et al., J. Craniofac. Surg. 6:421-423 (1995)). Buried modified Le Fort III midface advancements having cleft lip and palate with midface hypoplasia and Class III maloccluson have been performed (Cohen et al., Plast. Reconstr. Surg. 99:1421-1428 (1997)). In these cases, transverse maxillary expansion was performed with sagittal distraction and in one case serial distractors were used to provide vertical and horizontal distraction vectors. In other cases, a subtotal cranial vault reshaping and monobloc facial advancement was performed in a child who had Pfeiffer's syndrome and coreal exposure (Cohen et al., Plast. Reconstr. Surg, 101:1919-1924 (1998)). In that case, after 28 mm of distraction, the proptosis was largely corrected. Chin and Toth have reported Le Fort III advancement with gradual distraction using internal devices in a series of patients using a method of rapid distraction (Chin and Toth, Plast. Reconstr. Surg. 100:819-830 (1998)). Polley and Figueroa reported the management of maxialary deficiency in childhood and adolescence by performing distraction osteogenesis with an external adjustable, rigid distraction device to provide improvement in cleft lip, cleft palate and severe midface retrusion (Polley and Figueroa, J. Craniofac. Surg. 78:181-185 (1997); See generally Cohen, Seminars in Orthodontics, 5:52-58 (1999)).

Additional explanation of the conditions addressed by the present invention and, in some instances, more specific information about prior remedial practices is set forth together with the descriptions of exemplary embodiments of the present invention provided below.

BRIEF DESCRIPTION OF THE FIGURES

FIG. 7 is a conceptual diagram depicting the use of stabilizing means in a distraction procedure.

FIG. 8 is a conceptual diagram depicting the use of guiding means to direct the vector of distraction.

SUMMARY OF THE INVENTION

Figure 1:
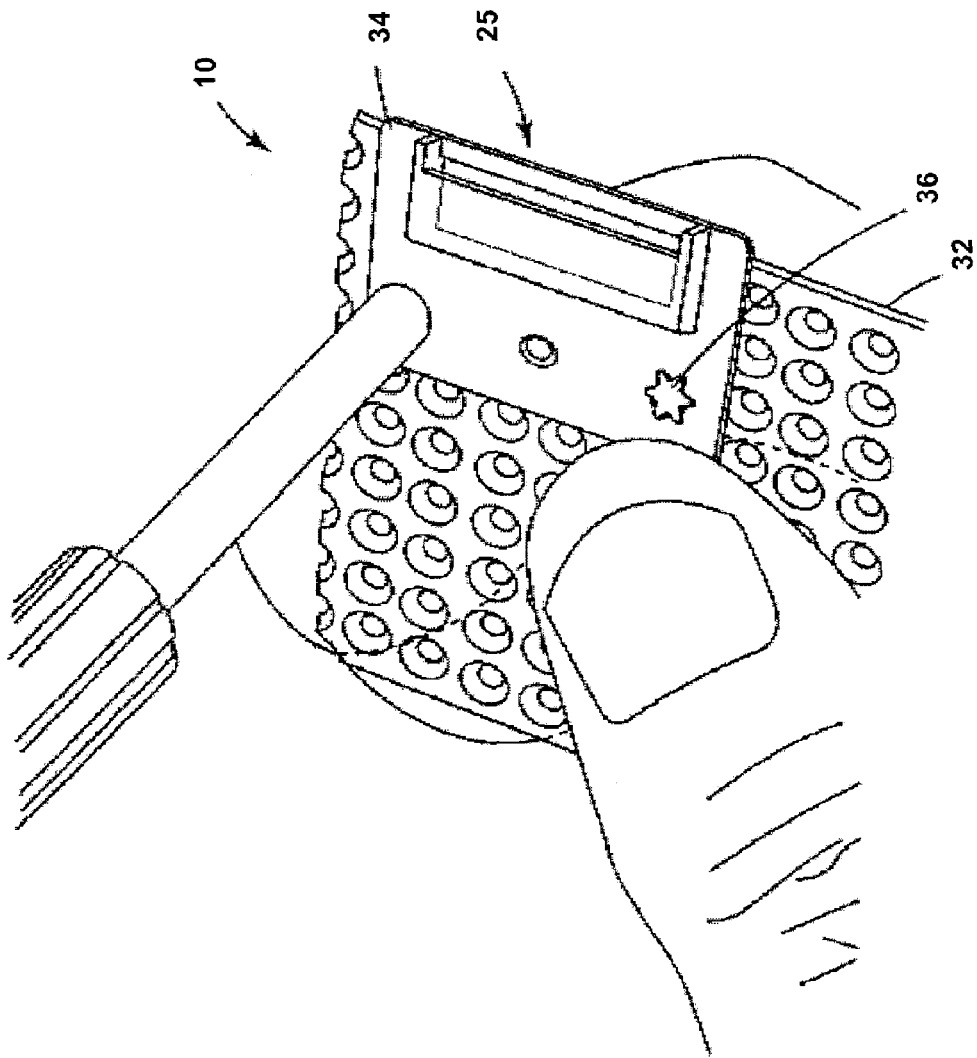
FIG. 1 is a perspective view depicting the two portions of a transmitting means being engaged using PLA/PGA screws.

The present invention recognizes that existing distraction devices have certain disadvantages, including the requirement to remove materials in the distraction device from the subjects body after distraction is completed. Depending on the location of distraction, this procedure can be of varying degrees of undesirability, such as due to difficulties of removal procedures and discomfort to the subject.

A first aspect of the present invention is a connective tissue distraction device comprising: a first transmitting means for transmitting force to a first tissue region and a second transmitting means for transmitting force to a second tissue region by contact with bone, expansion means for exerting force distracting said first transmitting means from said second transmitting means, wherein at least one of said first transmitting means, said second transmitting means and said expansion means comprises in whole or in part a biodegradable, bioerodible or bioresorbable material. Preferably two or more of these elements include in whole or in part such biodegradable, bioerodible or bioresorbable materials. Optionally, all three of these elements include in whole or in part such biodegradable, bioerodible or bioresorbable materials. In one preferred aspect of the present invention, the expansion means is not integral to at least one of or both of the first transmitting means or the second transmitting means.

A second aspect of the present invention is a method of distracting a first tissue region and a second tissue region, comprising: implanting the connective tissue distraction device of the present invention into a subject and distracting the first tissue region and the second tissue region.

A third aspect of the present invention is a device for stabilizing or early stabilization of distracted connective tissue that includes a biodegradable, bioerodible or bioresorbable material engaged on or near distracted connective tissue.

A fourth aspect of the present invention is a method for stabilizing or early stabilization of distracted connective tissue using a stabilizer that includes a biodegradable, bioerodible or bioresorbable material engaged on or near distracted connective tissue.

A fifth aspect of the present invention is a method for stabilizing or early stabilization of distracted connective tissue that includes providing biodegradable, bioerodible or bioresorbable materials, such as mesh, plates or macroporous plates at or near the site of distraction before, during or after distraction procedures such that protected bone regeneration of the distraction callus can is accentuated.

The methods and devices of the present invention utilize small single or multiple action expansion structures attached to anchoring or pressure exerting members gradually to distract bone or other connective tissue in order to increase tissue length and mass. Generally, at least one of the members in each device is fixed in place, such as with screws passing into bone, by attachment to teeth, with staples passing into bone, using appropriate glues or adhesives, or by engaging another member of the device of the present invention. Such fixing means, methods or structures, such as pins, screws or staples, can include in whole or in part biodegradable, bioerodible or bioresorbable materials. In addition, at least a portion of at least one member in each apparatus is preferably at made in whole or in part made of biodegradable, bioerodible or bioresorbable material. At least a portion of the apparatus of the present invention can be positioned subcutaneously or inside the patient's mouth in the case of intraoral or partially intraoral devices, thereby avoiding the need to penetrate the cheek. Preferably, the only portion of the device that is present outside of the body of a subject is a portion of an activating means that is used to actuate a device of the present invention to alter the spacial relationship of at least two members of an apparatus of the present invention. Portions or all or most such intraoral devices are positioned under the soft tissue that overlies bone being corrected. At other craniofacial sites, the entire device is positioned under overlying soft tissue, with a very small window or penetration through which the expansion mechanism is manipulated. Preferably, biodegradable, bioerodible or bioresorbable materials are provided under soft tissues rather than external to the subject, but that need not be the case. For example, certain biodegradable, bioerodible or bioresorbable materials may not be appropriate for use inside the buccal cavity due to moisture and biological activities, such as enzymatic activities, that may hasten the erosion of such materials. However, certain biodegradable, bioerodible or bioresorbable materials may be well-suited to extend external of the skin surface, such as in the cranio-facial region. For example, means to manipulate expansion means may be made of such biodegradable, bioerodible or bioresorbable materials and can external to the skin surface, such as through the scalp, such as behind an ear.

The use of the devices of the present invention reduces the physical and emotional trauma resulting from the distraction procedure and visibility of the distraction apparatus, reduces scarring, and permits distraction corrective procedures to be performed that were not previously possible. The present invention permits treatment of a wider variety of craniofacial deformities than was previously possible, including deformities of both traumatic and congenital origin, where greater bone length or mass, or additional other connective tissue, is required in a particular area.

As will be readily understood by those skilled in the art, a wide variety of conditions, typically involving congenital deformities, can result in the need for greater bone length or the presence of more bone or other connective tissue in a particular area. The exact nature of such conditions will vary widely from patient to patient, requiring that the geometry of the embodiments of the present invention described below be modified to accommodate the condition being addressed. The articles of manufacture and methods of the present invention can be used in any distraction procedure, including bone, preferably, but not limited to the craniofacial region and long bones, such as arm and leg.

The structures of the devices and practice of the techniques of the present invention will be more fully understood by reference to the following figures and detailed descriptions of the embodiments of the invention illustrated in these figures.

DETAILED DESCRIPTION OF THE INVENTION

Definitions

Unless defined otherwise, all technical and scientific terms used herein have the same meaning as commonly understood by one of ordinary skill in the art to which this invention belongs. Where a term is provided in the singular, the inventors also contemplate the plural of that term.

"Connective tissue" as used herein shall mean the tissue that binds together and supports the various structures of the body. In particular, "connective tissue" includes collagenous, elastic, mucous, reticular, and cartilaginous tissues, and preferably includes osseous tissue and bone.

A "transmitting means" refers to a structure that is preferably attached to a tissue region that is to be involved in a distraction procedure. The transmitting means can be made of any appropriate materials, including, but not limited to metals, ceramics, glass, bioglass, biodegradable, bioerodible, bioresorable materials and the like. Preferably, a transmitting means is made of a biodegradable, bioerodible or bioresorbable material, such as the material described in U.S. Pat. No. 5,919,234 to Lemperle et al., issued Jul. 6, 1999, and as available from MacroPore (San Diego, Calif.). Additional materials include lactic acid polymers as they are known in the art, such as PLAGA or PLA/PGA (poly-(lactic acid-glycolic acid)). Any appropriate biodegradable, bioerodible or bioresorbable materials can be used, so long as they have the desired characteristics, including biocompatablility and strength. Although the materials described in U.S. Pat. No. 5,919,234 are perforated, that is not a requirement of the present invention. Additional materials, such as PLA/PGA can also be used. Moreover, a transmitting means is preferably heat malleable such that the material is malleable at a temperature above that of the normal body temperature (such as a glass transition temperature at about 55° C. to 57° C. or greater, though the invention is not limited to such ranges of temperatures) and is rigid at body temperature (such as about 55° C. to 57° C. or less, though the invention is not limited to such ranges of temperature). The glass transition temperature of the material is preferably such that the malleable material, when contacted with a tissue or organ, that tissue or organ is not appreciably damaged.

Figure 2:
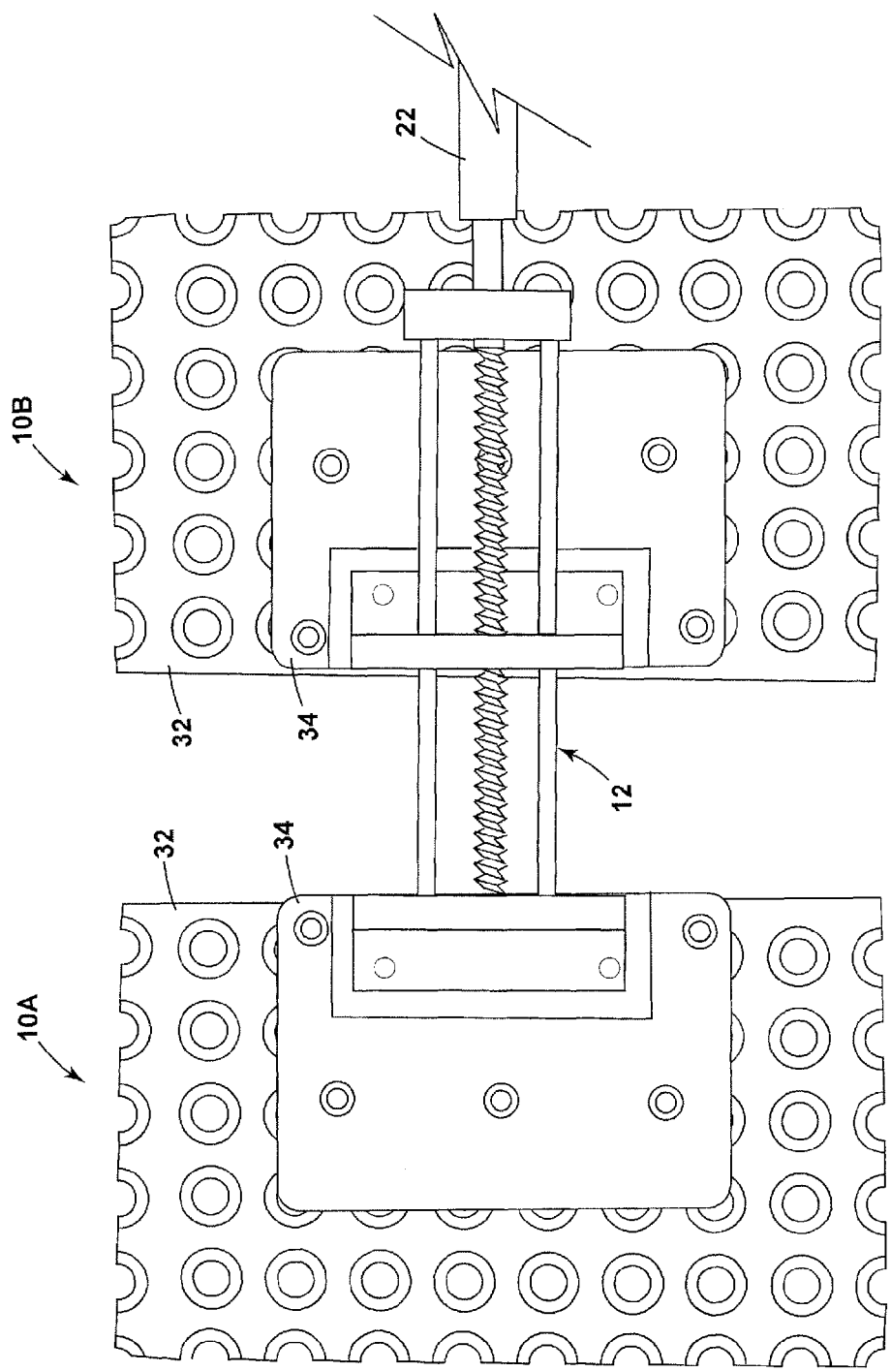
FIG. 2 is a plan view depicting two transmitting means of FIG. 1 engaged with an expansion means.

A transmitting means 10A, 10B (collectively 10) can be made of one or more components that can be engaged to form a transmitting means, such as set forth in FIGS. 1 and 2. The transmitting means preferably engages an expansion means 12 such that distraction is enabled by separating a first transmitting means 10A from a second transmitting means 10B by an expansion means 12 such as set forth in FIG. 2.

The transmitting means can be of any appropriate configuration, such as, for example, plates, stents, meshes or implants of any appropriate configuration. The transmitting means can have any appropriate shape, such as circular, oblong, polygonal, square or rectangular and can be cut to fit using appropriate cutting devices, including shearing devices such as scissors, or heating devices, such as a wire heated to an appropriate temperature to cut or trim the transmitting means. A transmitting means can be attached to a tissue region using any appropriate attachment structures, devices or means, such as, for example, screws, staples, tacks, pin, nails or implants of any appropriate configuration or the like, wherein such materials can be made of any appropriate material, preferably made at least in part of a biodegradable, bioerodible or bioresorbable material.

A "tissue region" includes a region of tissue to which an transmitting means is attached by an appropriate method, device or structure. Preferably, two tissue regions are adjacent to a site to be distracted. Preferably, a tissue region is a connective tissue, more preferably bone.

An "expansion means" refers to a device for expanding or contracting at least two transmitting means of the present invention. Preferably, the expansion means is a screw expansion mechanism. One skilled in the art would recognize that other mechanisms, either alone or in combination, such as, for example, ratchets, worm-screws, sliding devices, unidirectional sliding devices bidirectional sliding devices, multi-vector sliding devices, rack and pinion devices worm gears and the like can be used. The expansion means can be made of any appropriate materials, including, but not limited to metals, ceramics, glass, bioglass, biodegradable, bioerodible, bioresorable materials and the like. Preferably, a transmitting means is made of a biodegradable, bioerodible or bioresorbable material, such as the material described in U.S. Pat. No. 5,919,234 to Lemperle et al., issued Jul. 6, 1999, and as available from Macropore (San Diego, Calif.). Additional materials include lactic acid polymers as they are known in the art, such as PLAGA or PLA/PGA (poly-(lactic acid-glycolic acid)). Any appropriate biodegradable, bioerodible or bioresorabable materials can be used, so long as they have the desired characteristics, including biocompatablility and strength. Although the materials described in U.S. Pat. No. 5,919,234 are perforated, that is not a requirement of the present invention. Moreover, an expansion means is preferably heat malleable such that the material is malleable at a temperature above that of the normal body temperature (such as a glass transition temperature at about 55 C. to 57 C. or greater, though the invention is not limited to such ranges of temperatures) and is rigid at body temperature (such as about 55° C. to 57° C. or less, though the invention is not limited to such ranges of temperature). The glass transition temperature of the material is preferably such that the malleable material, when contacted with a tissue or organ, that tissue or organ is not appreciably damaged.

"Biodegradable" refers to a structure or material that, over time, can be removed by biological action within the body of a subject such as they are known in the art or later developed. Biodegradable material can include a bioactive compound, such as a pharmaceutical composition, a protein, a peptide, a nucleic acid molecule or a small molecule. Such bioactive compounds preferably have desirable activities associated with distraction procedures, such as growth factors of various types, bone morphogenic proteins, antibiotics or other compounds to improve or hasten the bone consolidation period or to decrease the time of distraction. These bioactive compounds can be leached from the biodegradable materials over time or be released as the biodegradable materials is removed by biological action.

"Bioerodible" refers to a structure or material that, over time, can be at least partially removed by biological action within the body of a subject. Preferably, bioerodible materials are removed from the body of a subject by biological action within between about one month to about one year, preferably between about three months and about nine months of implantation such as they are known in the art or later developed. Bioerodible material can include a bioactive compound, such as a pharmaceutical composition, a protein, a peptide, a nucleic acid molecule or a small molecule. Such bioactive compounds preferably have desirable activities associated with distraction procedures, such as growth factors of various types, bone morphogenic proteins, antibiotics or other compounds to improve or hasten the bone consolidation period or to decrease the time of distraction. These bioactive compounds can be leached from the bioerodible materials over time or be released as the biodegradable materials is removed by biological action.

"Bioresorbable" refers to a structure or material that, over time, can be at least partially removed by biological action within the body of a subject. Preferably, bioresorbable materials are at least partially removed from the body of a subject by biological action within between about one year and about ten years, preferably between about two years and about five years of implantation such as they are known in the art or later developed. Bioresorbable material can include a bioactive compound, such as a pharmaceutical composition, a protein, a peptide, a nucleic acid molecule or a small molecule. Such bioactive compounds preferably have desirable activities associated with distraction procedures, such as growth factors of various types, bone morphogenic proteins, antibiotics or other compounds to improve or hasten the bone consolidation period or to decrease the time of distraction. These bioactive compounds can be leached from the bioresorbable materials over time or be released as the biodegradable materials is removed by biological action.

Biodegradable materials, bioerodible materials and bioresorbable materials for use in the present invention can be selected from those known in the art or later developed based on their particular biological properties and physical properties. For example, materials preferably are biocompatible in that they do not stimulate a sustained or significant adverse biological response, such as an immunological response, such as an undesirable macrophage response. Such materials can be selected using methods known in the art, such as implantation into test animals or reviews of the literature. Materials preferably have appropriate tensile strength to withstand the stressed generated during distraction. Such materials can be selected using appropriate methods, such as strength determinations or reviews of the literature.

A variety of materials, including polymers such as synthetic polymers or natural polymers, can be suitable for use in the present invention. For example, polymers of the following classes are preferred: bioabsorbable bi-component polymers, bacterial polymers and copolymers such as poly-beta-hydroxy alkonates, polyurethanes, fiber reinforced polymers, self-reinforced polymers, and alpha-hydroxy carbonic acids. Preferred polymers can also include: Polymers issued from glycolic acid and lactic acids (PLAGA or PLA/PGA) (Vert et al., J. Controlled Release 53:85-92 (1998); polylactic acid (J. Oral Maxillofac. Surg. 56:616-626 (1998); collagens, aliphatic polyesters, poly(glycolic acid), poly(lactic acid), poly (epsiloncaprolactone) (Hutmacher et al., Int. J. Oral Maxillofac. Implants 11:667-678 (1996); coral/poly(DL-lactic acid) (Li et al., J. Biomater. Sci. Polym. Ed. 7:817-827 (1996); lactic acid polymers (Merlox et al., Rev. Chir. Orthop. Reparatrice Appar. Mot 81:433-444 (1995); copolymer 85/15 D,L lactide/glycolide (Balch et al., Arthroscopy 15:691-708 (1999); McGuie et al., Arthroscopy 15:463-473 (1999); Kumar et al., J. Craniofac. Surg. 8:97-99 (1997); Pietrazak et al., J. Craniofac. Surg. 8:92-96 (1997); Sinha et al., Drug Dev. Ind. Pharm 24:1129-1138 (1998); Tharanon et al., J. Craniofac. Surg. 9:441-444 (1998). Preferred polymers are of the class of polyhyproxyorthoesters as supplied by Boehringer Ingelheim.

Additional materials, such as polymers, that may be suitable for use in the present invention are described in the patent literature: U.S. Pat. No. 5,919,234 to Lemperle, issued Jul. 6, 1999; U.S. Pat. No. 5,935,594, issued to Ringeisen et al., issued Aug. 10, 1999; U.S. Pat. No. 5,935,594 to Ringeisen et al., issued Aug. 10, 1999; U.S. Pat. No. 5,876,452 to Athanasiou et al., issued Mar. 2, 1999; U.S. Pat. No. 5,766,710 to Turnlund et al., issued Jun. 16, 1998; U.S. Pat. No. 5,981,619 to Shikinami et al., issued Nov. 9, 1999 (cyrstalline thermoplastic polymer material, polylactic acid, polyglycolic acid, lactic acidglycolic acid copolymer and polydioxanone, hydroxylapatite (synthetic or natural, optionally in small amounts); U.S. Pat. No. 5,866,155 to Laurencin et al., issued Feb. 2, 1999 (syntheitic hydroxyapatite, tricalcium phosphate); U.S. Pat. No. 5,697,976 to Chesterfield et al., issued Dec. 16, 1997 (polymethylmethacrylate, polymeric hydroxyethylmethacrylate); U.S. Pat. No. 5,876,452 to Athanasiou et al., issued Mar. 2, 1999 (polyanhydrides, poly(ortho esters), aliphatic polyesters, polylactic acid, polyglycolic/polylactic acid mono-and-copolymers); U.S. Pat. No. 5,252,523 to Beall et al., issued Oct. 12, 1993 (bioabsorbable chlorophosphate and glass-polymer blends); U.S. Pat. No. 5,997,568 to Liu (dioxanone articles, Dexon, Vicryl and Polysorb materials))

A "subject" refers to a human or non-human subject. Non-human subjects can include experimental, test, agricultural, entertainment or companion animals.

"Early stabilizing" refers to the stabilization of distracted connective tissue at a time earlier that expected. Early stabilization can be accomplished using methods of the present invention. Such stabilization can be accomplished, for example, by the early formation of distracted tissue, early differentiation of distracted tissue, or in the case of bone, early mineralization of tissue.

"Distracted connective tissue" refers to the tissue formed during distraction procedure. In the case of bone, distracted connective tissue tends to form a somewhat unstructured, and thus soft, mass, which often takes time to strengthen, such as through mineralization.

Introduction

The present invention recognizes that existing distraction devices have certain disadvantages, including the requirement to remove materials in the distraction device from the subjects body after distraction is completed. Depending on the location of distraction, this procedure can be of varying degrees of undesirability.

As a non-limiting introduction to the breadth of the present invention, the present invention includes several general and useful aspects, including:

1) a connective tissue distraction device including a first transmitting means for transmitting force to a first tissue region and a second transmitting means for transmitting force to a second tissue region such as by contact with bone, expansion means for exerting force distracting said first transmitting means from said second transmitting means, wherein one, two or all of said first transmitting means, said second transmitting means and said expansion means comprises in whole or in part a biodegradable, bioerodible or bioresorbable material, preferably, the expansion means is not integral to one or both the first transmitting means or the second transmitting means;
2) a method of distracting a first tissue region and a second tissue region, including implanting the connective tissue distraction device of the present invention into a subject and distracting the first tissue region and the second tissue region;
3) a device for early stabilizing of distracted connective tissue that includes a biodegradable, bioerodible or bioresorbable material engaged on or near distracted connective tissue;
4) a method for early stabilizing of distracted connective tissue using a device that includes a biodegradable, bioerodible or bioresorbable material engaged on or near distracted connective tissue; and
5) a method for early stabilizing of distracted connective tissue that includes providing biodegradable, bioerodible or bioresorbable materials, such as mesh, plates or macroporous plates at or near the site of distraction before and/or during and/or after distraction procedures such that protected bone regeneration of the distraction callus can is accentuated.

I. A Connective Tissue Distraction Device

The present invention includes a connective tissue distraction device that includes a first transmitting means for transmitting force to a first tissue region, second transmitting means for transmitting force to a second tissue region and expansion means for exerting force distracting said first transmitting means from said second transmitting means. Preferably, one, two or all of said first transmitting means, said second transmitting means and said expansion means comprises in whole or in part a biodegradable, bioerodible or bioresorbable material. Optionally, the expansion means is not integral to one or both of the first transmitting means or the second transmitting means.

The first transmitting means and/or the second transmitting means can be the same or different in any regard, including size, shape and materials. The transmitting means can include a structure for attachment to a tissue region, such as a connective tissue such as bone. Such structures can include at least in part a biodegradable, bioerodible or bioresorbable material. Such structures can take any appropriate configuration such as those as discussed herein, but preferably include, for example, a plate, including a macroporous plate or a mesh. The structure for attachment to a connective tissue is attached to a tissue region via at least one appropriate attaching device, method or means. Preferred attaching structures include screws, staples, pins or stents. The attaching structures are preferably at least in part biodegradable, bioerodible or bioresorbable material and may be adapted to any commercially available expansion means, including metallic expansion means, such as those provided by Leibinger (Carrollton, Tex.) or described in U.S. Pat. No. 5,129,903 to Luhr et al., issued Jul. 14, 1992 or U.S. Pat. No. 5,769,850 to Chin, issued Jun. 23, 1998.

The first transmitting means and the second transmitting means are preferably directly or indirectly engaged or reversibly or irreversibly engaged to at least one expansion means. The expansion means can be any appropriate device or structure such as those discussed herein, preferably a screw actuated expansion mechanism, ratchet or sliding plates. Preferably, the expansion means includes in whole or in part a biodegradable, bioerodible or bioresorbable material. The expansion means can be modulated to draw the first transmitting means closer or further away from the second transmitting means. In doing so, the first tissue region and the second tissue region are brought closer together or further away. Alternatively, a transmitting means and an expansion means can be combined into a single structure, such that there is 1) a transmitting means and 2) a transmitting means and an expansion means that forms the connective tissue distraction device.

Figure 10:
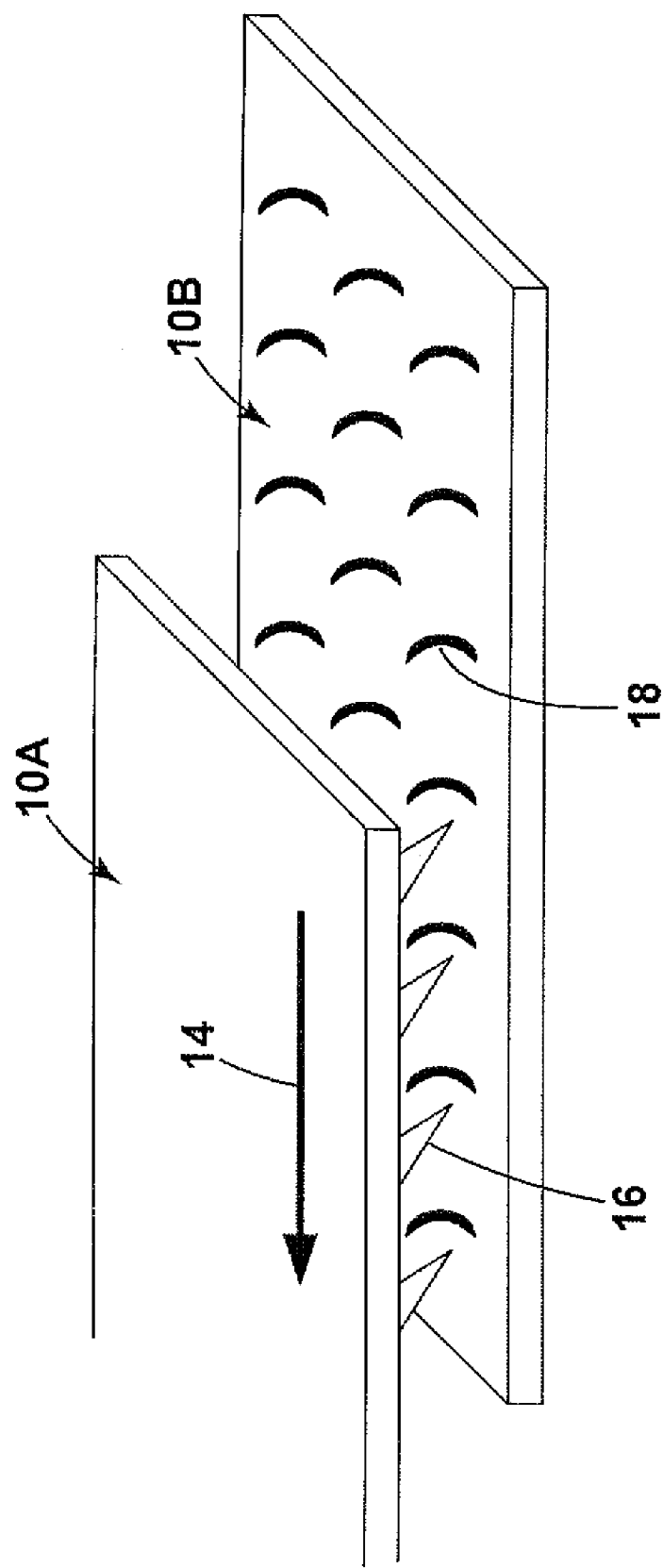
FIG. 10 is a conceptual diagram depicting the use of engaging structures, such as in a "shark's tooth" configuration, that allows members of the distraction device to slide against each other in a unidirectional manner, which can also serve to stabilize the distraction device itself.

In one aspect of the present invention, the first transmitting means 10A and the second transmitting means 10B comprise structures that allow the transmitting means 10 to slide unidirectional across each other. The two transmitting means 10 can slide along a single vector 14 or multiple vectors based on the particular structures used. For example, the first transmitting means 10A can comprise engaging structures designed to engage mating structures on the second transmitting means 10B. For example, the first transmitting means 10A can comprise a plurality of indentations, hole, protrusions, "shark's teeth" or other structures that can engage mating structures on the second transmitting means 10B such as indentations, holes, protrusions or other structures. Preferably, the engaging structures are indentations or holes 16 and the mating structures are protrusions such as pins or shark's teeth structures 18. Alternatively, the engaging structure and the mating structure are shark's teeth structures. As the two transmitting means slide across each other in one direction 14, they engage such that they preferentially do not slide in a different direction. One preferred example of the aspect of the invention is depicted in FIG. 10.

In another aspect of the present invention, the connective tissue distraction device includes guiding means 20 to allow distraction to proceed along a pre-determined vector. For example, a guiding means can include a variety of structures to engage at least one portion of at least one transmitting means, such as tongue and groove configurations. The guiding means are preferable made at least in part of a biodegradable, bioerodible or bioresorbable material. One preferred example of this aspect of the present invention is provided in FIG. 8.

The connective tissue distraction device can further include an activation means to modulate the expansion means. The activation means can be at least in part external to the subject such that the distraction device can be adjusted without invasive procedures. The activation means can be adjusted using additional materials, such as turn-keys, that activate the expansion means. The activation means can directly or indirectly engage the expansion means, such as by having additional structures between the expansion means and the activation means (Leibinger MID System, Scientific Documentation, Modular Internal Distraction System, Howmedica Leibinger (1998)).

In one aspect of the present invention, the activation means 22 can be engaged with the expansion means 12 at will, such as where the activation means can engage the expansion means while within the subject and then be removed at will. Preferably, the activation means is engaged with the expansion means only for activating the expansion means and then is removed. The tissues surrounding the expansion means can be structured using surgical methods known in the art so that the activating means and the expansion means can be reversibly engaged. While so engaged, the activation means can activate the expansion means. In one aspect of the present invention, the activation means can include a gear reduction structure, such as between about 1:2 and about 1:50, preferably between about 1:5 and about 1:20, so that relatively large movements in the activation means result in relatively smaller movements in the expansion means. The use of such gear reduction allows for accuracy and reproducibility in the distances chosen for distraction procedures. When the activation means is removable at will, it is preferred that the transmitting means and/or expansion means engage using structures 16, 18 that encourage unidirectional displacement, such as provided in FIG. 10.

Figure 3:
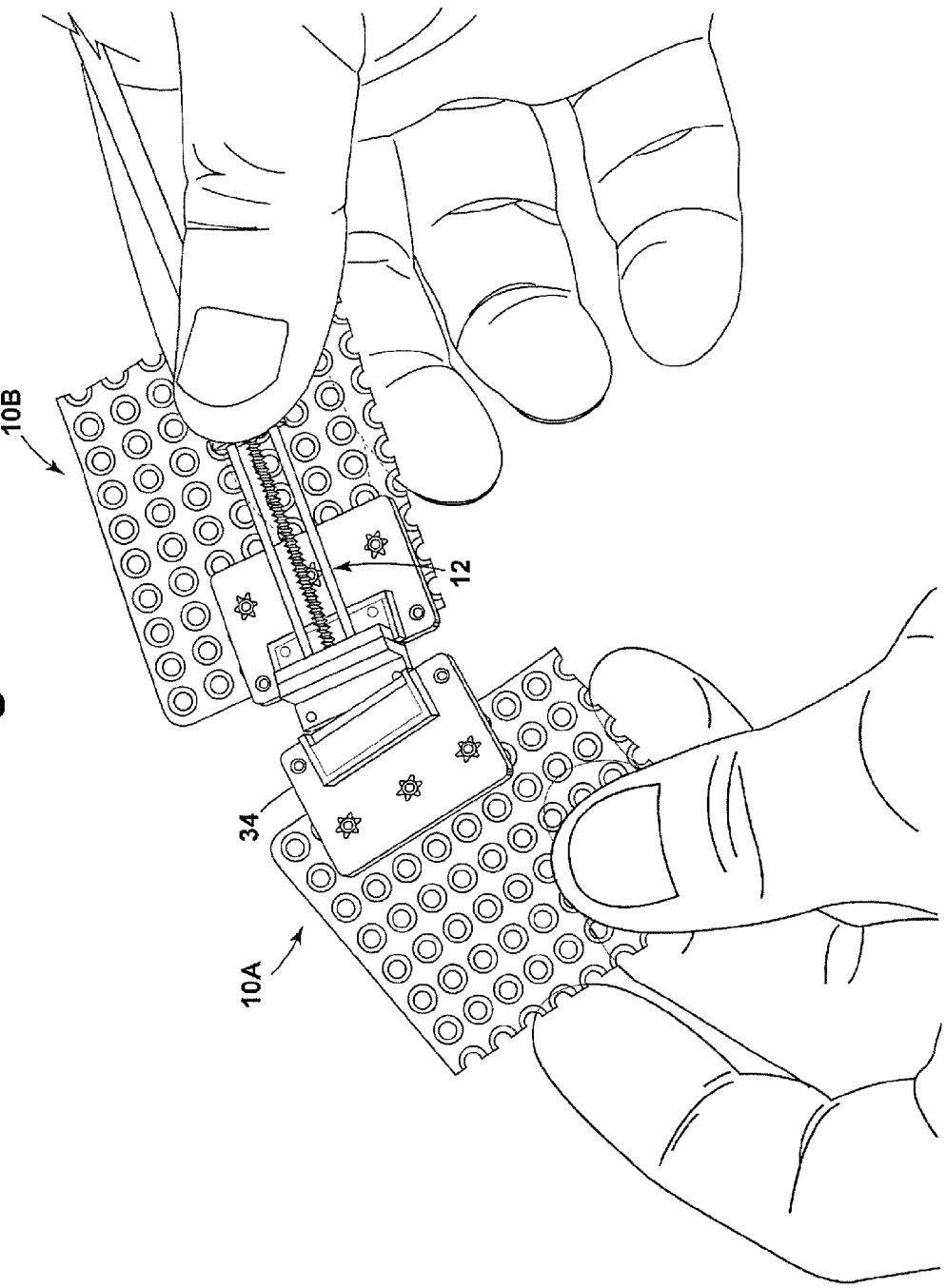
FIG. 3 is a perspective view depicting the nature of the engagement of the transmitting means and the expansion means as reversible.
Figure 5:
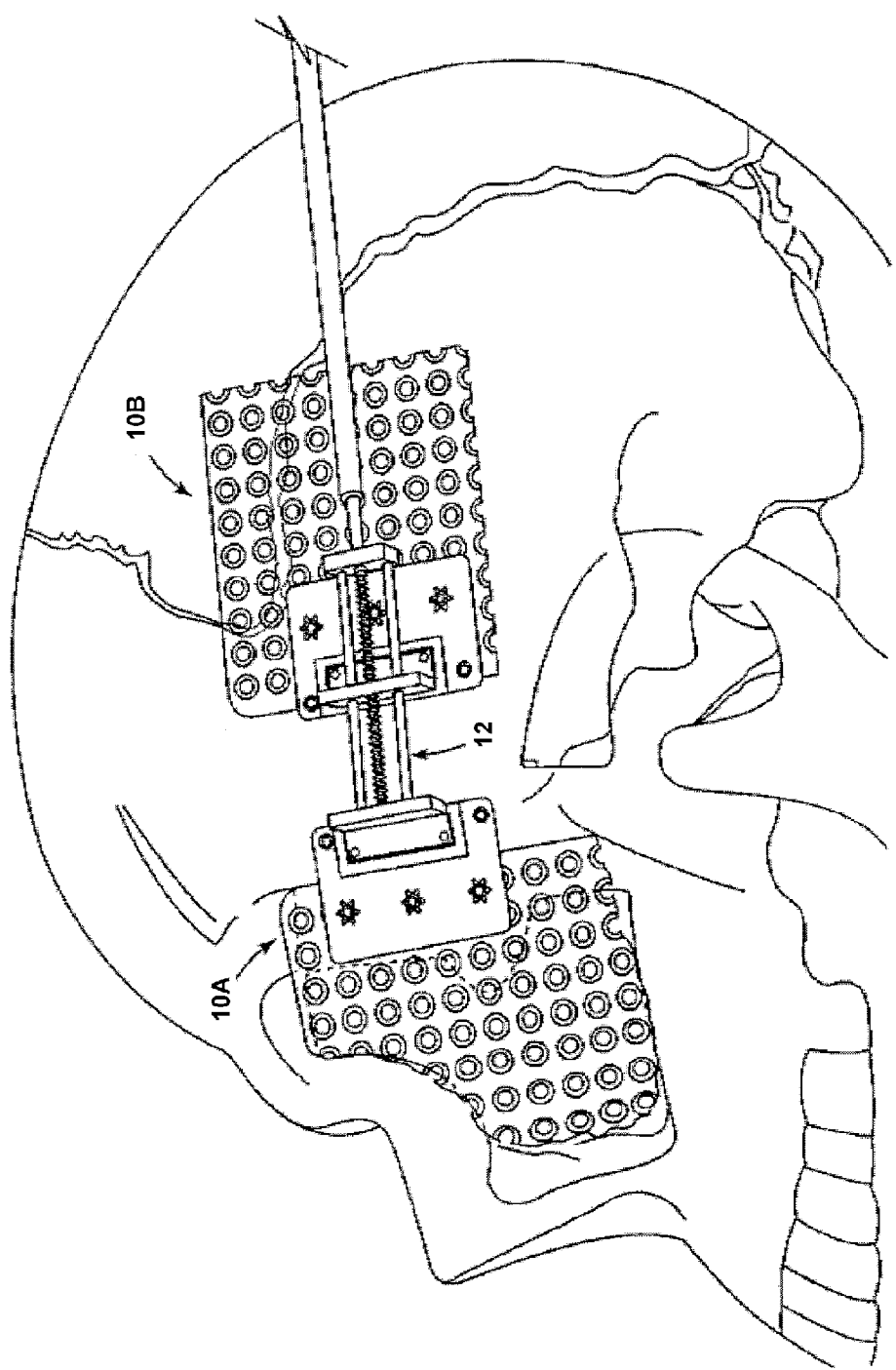
FIG. 5 is a perspective view depicting the distraction device after distraction has taken place. This figure depicts a mock-up skull, thus the distraction space has not been filled with distraction tissue. At the point in the procedure, the expansion means would be removed by disengaging the expansion means from the transmitting means, such as by engaging the activation means to decrease the length of the expansion device. The expansion means can be removed using surgical procedures, preferably endoscopic procedures. If the expansion means is made in whole or in part of biodegradable, bioerodible or bioresorbable materials, then the expansion means can optionally be removed. Optionally, at least one stabilizer can be inserted into, over or around the expansion space and appropriately secured such that the distracted tissue is mechanically stabilized. Such stabilizer(s) are preferably made at least in part of biodegradable, bioerodible or bioresorbable material, such as PLA/PGA, preferably macroporous PLA/PGA.
Figure 6A:
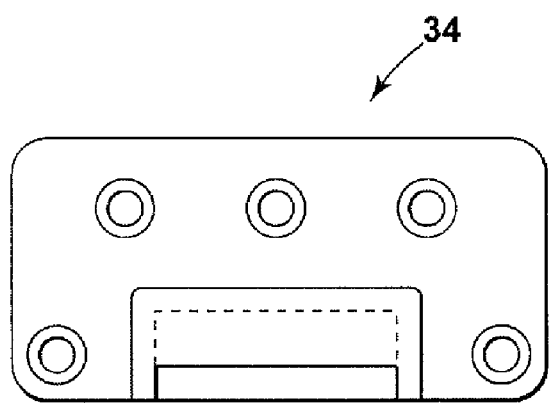
FIGS. 6A, 6B and 6C are top, bottom and side views depicting a flange-engaging structure of a transmitting means of one aspect of the present invention that includes structures to engage an expansion means.
Figure 6C:
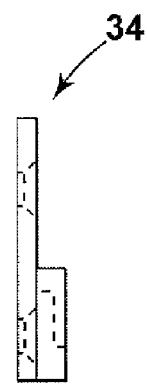
Figure 6B:

FIGS. 3 and 5 show a removable expansion means 12 that includes a screw expansion mechanism having a proximal end and a distal end. The proximal end includes a first L-shaped flange having a first vertical plate that receives the screw expansion mechanism and a first horizontal plate that is substantially perpendicular to the first vertical plate and that engages the first flange engagement structure of the first transmitting means. As shown in FIGS. 3, 5 and 6A-6C, the first flange engagement structure is sized to receive the first horizontal plate. The distal end of the expansion means 12 includes a second L-shaped flange having a second vertical plate connected to the distal end of the screw expansion mechanism and a second horizontal plate that is substantially perpendicular to the second vertical plate and that engages the second flange engagement structure of the second transmitting means. As shown in FIGS. 3, 5 and 6A-6C, the second flange engagement structure is sized to receive the second horizontal plate.

FIGS. 3 and 5 show a removable expansion structure 12 that includes a screw expansion mechanism. The expansion structure 12 includes a proximal end having a first L-shaped flange having a first vertical plate that receives the screw expansion mechanism and a first horizontal plate that is substantially perpendicular to the first vertical plate and that engages a first slot of the first transmitting structure. As shown in FIGS. 3, 5 and 6A-6C, the first slot is sized to receive the first horizontal plate. The expansion structure 12 also includes a distal end having a second L-shaped flange having a second vertical plate connected to a distal end of the screw expansion mechanism and a second horizontal plate that is substantially perpendicular to the second vertical plate and that engages a second slot of the second transmitting structure. As shown in FIGS. 3, 5 and 6A-6C, the second slot is sized to receive the second horizontal plate.

The activation means 22 need not be permanently engaged with the expansion means. This is particularly true when the expansion means 12 is designed of biodegradable, bioerodible or bioresorbable material and intended to be left in the subject. Under those circumstances, the activation means is preferably not made of biodegradable, bioerodible or bioresorbable materials can be conveniently disengaged from the remainder of the distraction structure and removed. In this aspect, the portion of the distraction structure remaining within the subject comprises in whole or in part biodegradable, bioerodible or bioresorbable materials. In another aspect of the present invention, the activation means and expansion means are integral to each other can be disengage from one or more transmitting means and removed (see, FIGS. 1-3).

The present invention also includes a connective tissue distraction device of the present invention implanted in a subject. When implanted at least on part within the subject, it is preferable that the transmitting means and the expansion means are internal to the subject. When present, it is preferable that at least a portion of the activation means is external to the subject.

II A Method of Distraction

The present invention also includes a method of distracting a first tissue region and a second tissue region, comprising: implanting the connective tissue distraction device of the present invention into a subject and distracting the first tissue region and the second tissue region. The tissue regions are preferably separated, such as by an accident or by surgical procedures such that bone lengthening is planned and desired. Tissue regions, such as connective tissues including bone can be wholly or partially separated using methods known in the art, including osteotomy.

Figure 4:
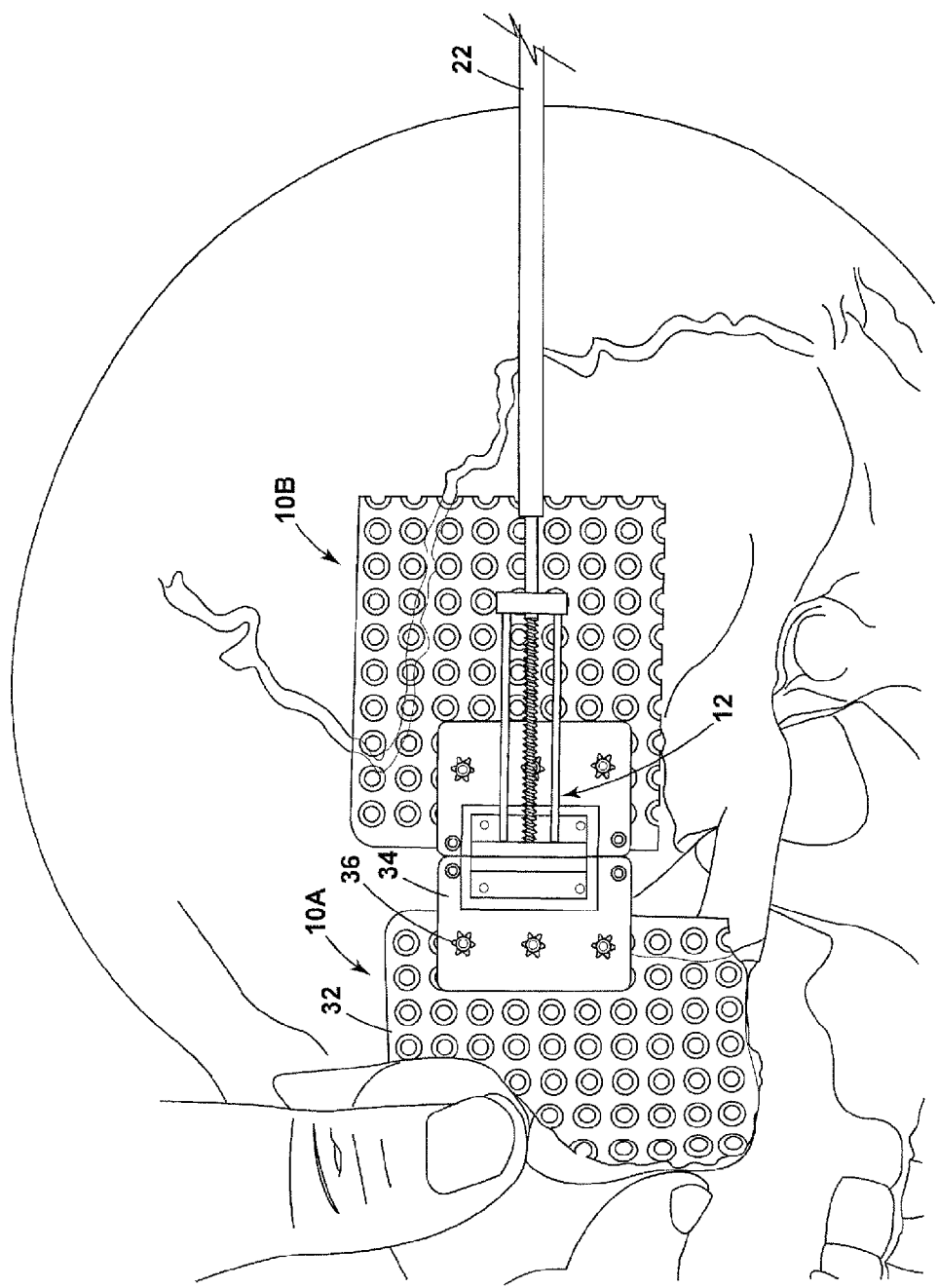
FIG. 4 is a perspective view depicting the distraction device in place at the site of osteotomy. The transmitting means are secured to the skull using PLA/PGA screws in holes drilled into the bone. During a distraction procedure, the implementation of the distraction device would be complete. Distraction would be accomplished by engaging the expansion means with an activation means to gradually increase the distraction distance.

As set forth in FIG. 4, the device of the present invention is appropriately engaged in the subject. The distraction device is then modulated using the expansion means 12 and optionally the activation means 22 to cause the tissue regions to become further apart. The speed and distance by which the tissue regions are separated by the distraction device are choices to be made by the surgeon based on the particular circumstances of a particular case. A rate of distraction of about 0.5 mm to about 1.0 mm twice a day is recommended. Distraction continues until the desired distraction distance has been achieved or circumstances dictate otherwise. Then, the freshly deposited tissue, when bone, is allowed to mineralize and thus strengthen.

In the present method, components of the distraction device that are not biodegradable, bioerodible or bioresorbable are preferably removed after distraction is completed. In preferred aspects of the present invention, the transmitting means are made of such biodegradable, bioerodible or bioresorbable materials and thus need not be removed. If the expansion device is not made of a biodegradable, bioerodible or bioresorbable materials, then that device can be removed by surgical or other methods. Preferably, the expansion means is reversed, such as by the activating means, to free the expansion means from the transmitting means. The expansion means can then be removed with minimal invasive procedures.

The activating means can be removed independently of the expansion means. This is particularly preferable if the expansion means is made of a biodegradable, bioerodible or bioresorbable material. In this instance, the expansion means and activating means are preferably reversibly engaged by an appropriate structure as they are known in the art, such as, for example, male-female coupling structures.

III Device for Stabilizing or Early Stabilization of Distracted Connective Tissue The present invention also includes a device for early stabilizing of distracted connective tissue. The device includes a stabilizer that includes at least in part a biodegradable, bioerodible or bioresorbable material engaged on or near distracted connective tissue. The distracted connective tissue is preferably bone, but can be other connective tissues. The stabilizer is preferably within a subject. Due to the biodegradable, bioerodible or bioresorbable material in the stabilizer, the stabilizer will be at least in part absorbed by the subject and not require additional surgical procedures.

One preferred aspect of the present invention includes a stabilizer made of a macroporous biodegradable material, such as through Macropore (San Diego). The device is preferably designed to engage at least one transmitting means such that space between transmitting means is spanned at least in part, preferably in whole, by the stabilizer. The stabilizer can be engaged with connective tissue, such as bone, using appropriate materials, preferably fasteners made at least in part of biodegradable, bioerodible or bioresorbable material. Preferably, the stabilizer replaces the expansion means when such means are note made of biodegradable, bioerodible or bioresorbable materials.

In one aspect of the present invention, the stabilizer replaces at least one transmitting means and an expansion means. For example, as shown in FIG. 8 the stabilizer would be designed to replace the distal (right) transmitting means and the expansion means by having a shape and size corresponding to the combination of the distal transmitting means: expansion means combination. As such, the stabilizer would have a flange that corresponds to the metal flange that engages the notch in the proximal (left) transmitting means 10A. As shown in FIG. 8 the stabilizer 24 would correspond to the combination in the right hand of the model. In this aspect of the invention, the distal transmitting means and expansion means would be removed and replaced with the stabilizer. Optionally, the stabilizer would be designed to replace the proximal transmitting means. This is the choice of the surgeon, such as on the invasive nature of the procedure. In the procedure depicted in FIGS. 4 and 5, for example, the procedure is much less invasive to remove or alter the distal transmitting means and as such is preferably over removing or altering the proximal means.

Optionally, the stabilizer can take the shape of at least a portion of the combination of the distal transmitting means: expansion means combination. In that instance, the distal transmitting means need not be removed, the expansion means is removed, and the stabilizer is engaged to the connective tissue using appropriate attaching structures 26. Optionally, the stabilizer would be designed to take the shape of at least a portion of the combination of the proximal transmitting means: expansion means combination. This is the choice of the surgeon, such as on the invasive nature of the procedure. In the procedure depicted in FIGS. 4 and 5, for example, the procedure is much less invasive to modulate the area of the distal transmitting means and as opposed to the area of the proximal transmitting means.

IV Method for Stabilizing or Early Stabilization of Distracted Connective Tissue Using a Stabilizer Another aspect of the present invention is a method for early stabilizing of distracted connective tissue that includes performing distraction on a subject using a distraction device and engaging a stabilizer of the present invention with at least one of said transmitting means. Preferably, the stabilizer includes at least in part a biodegradable, bioerodible or bioresorbable material, more preferably of macroporous or other material that promotes bone formation and strengthening, such as described in U.S. Pat. No. 5,919,234, PLA/PGA or available from a variety of commercial sources, such as Macropore (San Diego, Calif.). Preferably, the stabilizer is engaged on or near distracted connective tissue such that distracted tissue is supported and stabilized and allowed to strengthen. The stabilizer can be engaged with a tissue region using appropriate attachment devices as described herein, which are preferably made at least in part from biodegradable, bioerodible or bioresorbable materials. The tissue region preferably comprises connective tissue, such as bone.

One preferred aspect of the present invention has its basis in the procedure depicted in FIGS. 4 and 5. Distraction is carried out as set forth in the depicted procedure, resulting in the distraction set forth in FIG. 5. The expansion means 12 is removed, which results in unsupported expansion tissue that is relatively weak. A stabilizer 24 of the present invention, as discussed above, can be engaged in a variety of configurations to replace the expansion means at least in part and/or at least a portion of at least one of the transmitting means. One preferred aspect of this invention is a stabilizer made of macroporous PLA/PGA that corresponds roughly to the size and shape of the distal transmitting means, the distracted space, and the expansion means, including the flange of the expansion means that engages the slot 25 of the proximal transmitting means 10A. The distal transmitting means is optionally removed, the stabilizer engaged, and the stabilizer preferably engaged with connective tissue at the location of the distal transmitting means using appropriate attachment structures 26 or devices as described herein. As discussed above, the choice of modulating the proximal or distal transmitting means is that of the surgeon based on the particular circumstances of the case at hand, including the relative invasive nature of the locus of the transmitting means, the safety of the procedure, and the desired result.

In the alternative, a stabilizer of the present invention can be designed to be of a variety of shapes, such as strips, that span the distracted space. In that instance, the strips are positioned to span the distracted space and are secured to the tissue, such as bone on either side of the distracted space. This step can be performed before or after the expansion device is removed. Such materials are preferably made of macroporous PLA/PGA.

Furthermore, at least one stabilizer can be included in the distraction device. The stabilizer is preferably made at least in part of biodegradable, bioerodible or bioresorbable material, such as PLA/PGA, preferably macroporous strips or meshes of that material. The stabilizer can be fashioned to be attached to one side of the distraction gap and allowed to slide relatively unabated during the distraction procedure. After distraction is completed, the stabilizer can be attached to the other side of the distraction gap 30. One preferred example of this aspect of the present invention is depicted in FIG. 7.

V Method for Stabilizing or Early Stabilization of Distracted Connective Tissue using Biodegradable, Bioresorbable or Bioerodible Materials Another aspect of the present invention is a method for early stabilizing of distracted connective tissue that includes providing biodegradable, bioerodible or bioresorbable materials, such as mesh, plates or macroporous plates at or near the site of distraction before and/or during and/or after distraction procedures preferably such that protected bone regeneration of the distraction callus can is accentuated.

1. Stabilizing Distracted Connective Tissue—Pre-Distraction Procedures

One method of the present invention is a method for early stabilizing of distracted connective tissue, including: providing at least one biodegradable, bioerodible or bioresorbable material at or near the site of distraction before a distraction procedure take place and performing distraction. The material is preferably a material that encourages bone growth, development or strengthening, such as macroporous materials or meshes of materials (such as those described in U.S.

Pat. No. 5,919,234, preferably made of PLA/PGA). The material is preferably malleable, such as heat malleable or chemical malleable, and can also optionally have shape memory.

In operation, the site to be distracted is covered at least in part with the material such that during distraction soft tissues and other materials are at least preferentially at least partially kept out of the distraction space. Such materials are fashioned to the distraction site before or after osteotomy procedures, preferably after such procedures. A distraction device, either of the present invention or otherwise, is then mounted to the distraction site and distraction takes place as appropriate for the location of the distraction and the type of device used. Distraction devices made entirely of metal such as they are known in the art (see, for example, Leibinger Mid-System documentation 90-02104 (12/98), Howmedia Leibinger, Carrollton, Tex., which is incorporated herein by reference) can be used, as well as the distraction devices of the present invention. Other distraction devices known in the art or later developed can also be used in these methods. The presence of these material is expected to aid in the speed of distraction. Although the inventors do not wish to be limited to any particular mechanism, enhanced speed of distraction may be attributable to increased speed of bone formation, increased mechanical stability provided by the material, or increased speed of mineralization of the distracted tissue. In one preferred aspect of the invention, the material can form layers which slide against each other as distraction proceeds such that the distraction space is continually covered with material. In one aspect of this invention, for example, a rounded long bone is to be distracted, the first transmitting means can be a first cylinder and the second transmitting means can be a second cylinder, wherein the first cylinder and second cylinder overlap each other, such as two tubes of different diameters would. As distraction proceeds, the distraction space remains covered by the material that overlaps in the two cylinders. Of course, this procedure does not require the use of rounded long bones nor the use of cylindrical transmitting means and the procedure can be adapted to other configurations, shapes and locations.

Furthermore, at least one stabilizer can be included in the distraction device. The stabilizer is preferably made at least in part of biodegradable, bioerodible or bioresorbable material, such as PLA/PGA, preferably macroporous strips or meshes of that material. The stabilizer can be fashioned to be attached to one side of the distraction gap and allowed to slide relatively unabated during the distraction procedure. After distraction is completed, the stabilizer can be attached to the other side of the distraction gap.

2. Stabilizing Distracted Connective Tissue—During Distraction

A further method for early stabilizing of distracted connective tissue, including: providing biodegradable, bioerodible or bioresorbable materials at or near the site of distraction during distraction. The material is preferably a material that encourages bone growth, development or strengthening, such as macroporous materials or meshes of materials (such as those described in U.S. Pat. No. 5,919,234, preferably made of PLA/PGA). The material is preferably malleable, preferably heat malleable.

In operation, a distraction device is implanted at a distraction site the site to be distracted using methods appropriate for the site of distraction, the method of distraction and the distraction device chosen. The material can be attached to the site using methods and procedures described in U.S. Pat. No. 5,919,234. During the distraction procedure, especially if the distraction procedure is not progressing well, the distraction site, preferably including distraction tissue is covered at least in part with the material such that during the remainder of distraction soft tissues and other materials are preferentially at least partially kept out of the distraction space. Distraction devices made entirely of metal as known in the art can be used, as well as the distraction devices of the present invention. Other distraction devices known in the art or later developed can also be used in these methods. The presence of the material can aid in the speed of distraction. Although the inventors do not wish to be limited to any particular mechanism, the speed of distraction may be attributable to increased speed of bone formation, increased mechanical stability provided by the material, or increased speed of mineralization of the distracted tissue.

3. Stabilizing Distracted Connective Tissue—After Distraction

Another method for early stabilizing of distracted connective tissue, including: providing biodegradable, bioerodible or bioresorbable materials at or near the site of distraction after distraction has taken place. The material is preferably a material that encourages bone growth, development or strengthening, such as macroporous materials or meshes of materials (such as those described in U.S. Pat. No. 5,919,234, preferably made of PLA/PGA). The material is preferably malleable, preferably heat malleable.

In operation, the site that has been distracted is covered at least in part with the material such that soft tissues and other materials are preferentially at least partially kept out of the distraction space. Such materials are fashioned to the distraction site after distraction is completed. The materials can be fashioned to the location before or after the distraction device, or a portion thereof, if necessary, has been removed. Distraction devices made entirely of metal as known in the art can be used, as well as the distraction devices of the present invention. Other distraction devices known in the art or later developed can also be used in these methods. The presence of the material can aid in the speed of recovery after distraction is completed. Although the inventors do not wish to be limited to any particular mechanism, the speed of distraction may be attributable to increased speed of bone formation, increased mechanical stability provided by the material, or increased speed of mineralization of the distracted tissue.

VI Preferred Aspects of the Present Invention

This section described a variety of distraction devices wherein at least one of the elements of the device, including attachment devices, is made in whole or in part of a biodegradable, bioerodible or bioresorbable material. The choice of which elements of the distraction device which are to made in whole or in part of a biodegradable, bioerodible or bioresorbable material depends on the location of the element (such as in the buccal cavity, subcutaneously or in contact with bone) and the result desired by the surgeon and guided by the present disclosure and the state of the art. For example, the materials described in U.S. Pat. No. 5,919,234 may not be particularly well suited for the buccal cavity. Preferably, plates, support structures such as wires, and means for attaching structures to bone, such as staples, stents, pins and screws, are made in whole or in part of biodegradable, bioerodible or bioresorbable materials. Furthermore, expansion devices can optionally be made in whole or in part of such biodegradable, bioerodible or bioresorbable materials.

As will be readily appreciated by those skilled in the art, the exemplary embodiments of the present invention described herein are provided for the purpose of illustrating practice of the invention but are not intended to limit the scope of the following claims. Numerous modifications and improvements may be made to the invention without departing from the spirit and intent of the invention or scope of the claims.

The very nature of the human tissue formation problems the present invention addresses involves substantial variation from patient to patient and therefore requires adaptation of the invention to the needs of each patient. Additionally, a variety of known and yet to be developed materials can be used to practice the invention. Appropriate materials should have the needed mechanical properties and bio-compatibility for the uses described. Among such materials appropriate for various components of the invention are stainless steel, titanium, and various polymeric materials, including acrylic materials widely utilized in dental and orthodontic applications.

Commercially available plate components made of stainless steel, titanium, biodegradable, bioerodible or bioresorbable materials as well as other materials may be used for the plates described above. Examples of such components include the plate system components available from Synthes Ltd. (U.S.A.), Howmedica, Walter Lorenz Surgical Instruments, Inc., Leibinger, MacroPore and others. It will be preferable in some instances to replace the described plates (which normally cannot be left in the patient permanently) with implantable osseointegrated components to which the force exerting components of the present invention can be reattached multiple times.

Expansion mechanisms having different sizes and methods of action than those illustrated and described herein can also be used in practicing the present invention, and expansion mechanisms actuated otherwise than with screws may also be appropriate provided that they are sufficiently compact to permit intraoral or buried installation of the devices contemplated by the present invention and allow essentially or entirely non-invasive periodic incremental adjustment as described above. For instance, any of the expansion mechanisms, particularly including the expansion mechanism of buried distraction device, could utilize a bevel-gear actuated jackscrew mechanism so that rotation of an actuation screw by access to the end of its head coaxial with the screw results in expansion at right angles to the axis of the action screw. In the case of buried distraction device, this could permit the use of a smaller chimney penetrating the overlying soft tissue or would permit the actuation screw itself to protrude through an appropriately sleeved chimney to make it accessible for adjustment. Similarly, cam-acting, ratchet-acting or ratchet and pawl expansion mechanisms could be substituted for the screw-actuated mechanisms described above. As an alternative to all of these, fluidically actuated expansion mechanisms using pneumatic or hydraulic cylinders or bladder force-exerting mechanisms could also be used.

A. Intraoral, Internal Mandibular Bone Distraction Device

An intraoral, internal mandibular bone distraction device id positioned on a human mandible. A mandibular bone distraction device performs introral distraction osteogenesis of the mandible in patients with mandibular bone deficiency from a variety of etiologies including but not limited to: (1) Hemifacial microsomia; (2) Goldenhar's syndrome; and (3) Mandibular deficiency with retrognathism from any other cause.

The mandibular distraction device includes a first transmitting means that attaches to the teeth, such as by bonding or cementing using appropriate materials. The second transmitting means is preferably a plate that is rigidly attached to the mandibular ramus. The first transmitting means and the second transmitting means are engaged with an expansion means used to effect distraction.

The mandibular distraction device can utilize a miniature screw expansion mechanism as the expansion means. That expansion means can include a female slide that receives a male slide, which is moved relative to female slide by rotation of a double acting jack screw that has two oppositely threaded ends, one of which is received in a threaded hole in each slide. The jack screw has centrally located trans-axial holes into which a small pin may be inserted in order to rotate the screw. Screw expansion mechanisms are referred to as "expansion screws" and may be obtained in a variety of sizes and configurations from Dentaurum, Inc. 10 Pheasant Run, Newtown, Pa. 18940-1819; RMO Incorporated, P. O. Box 17085, Denver, Colo. 80217; and Turotech, P. O. Box 284, Wynnewood, Pa. 19096. Expansion means such as screw mechanisms may be used singly or in series or parallel where greater expansion is desired or other conditions dictate in this aspect or other aspects of the present invention.

Mandibular distraction device may be unilateral or bilateral where both sides of the mandible require lengthening. If the mandibular distraction device is bilateral, the first transmitting means may extend across all teeth in the mandible if such a configuration is appropriate.

With the patient under general anesthesia, the mandibular distraction device is inserted in the patient's mouth, the first transmitting means is attached, such as by bonding or cement, to the teeth and the plates are rigidly fixed to the mandible with screws after appropriate incisions in overlying soft tissue make the mandible surface accessible. The surgeon also performs a cut in the mandible or an osteotomy proximal to the mandibular dentition, and the bone is gradually distracted by periodically cranking the screw expansion device. Osteogenesis takes place by the principle of Ilizarov or bone lengthening, whereby new bone is formed in between the edges of the bones being gradually distracted.

As will be appreciated by those familiar with prior tissue distraction techniques, the mandibular distraction device eliminates external scars, is easily placed, avoids the need for tissue penetration on the female slide of the device by attachment to the teeth rather than to bone, avoids interference with intraoral structures and function because of its low profile and can be easily modified for other applications and situations.

B. Intraoral, Internal Maxillary-Zygomatic-Orbital Distraction Device

A variety of conditions result in malformation or improper growth of the maxillary-zygomatic-orbital region. For instance young patients with cleft lip and palate sometimes exhibit improper maxilla growth. Another embodiment of the present invention is an intraoral, internal maxillary-zygomatic-orbital distraction device. This device has a variety of applications in surgically assisting maxillary-zygomatic-orbital growth in three dimensions. By use of the maxillary-zygomatic-orbital distraction device, gradual distraction osteogenesis may obviate the need for surgery later or reduce its level of complexity.

The maxillary-zygomatic-orbital distraction device comprises a first transmitting means that is attached to teeth and the second transmitting means is a plate. The expansion means preferably comprises two screw expansion mechanisms that are positioned in the upper buccal sulci. One side of each of the screw expansion mechanisms is preferably attached to the first transmitting means affixed to the maxillary teeth with clasps and resin bonding material or bone cement. The other side of each expansion means is preferably attached to a second transmitting means that takes a form of a plate that is rigidly fixed to the maxilla, zygoma, cranium or orbit as is appropriate for the condition being treated. As described above in connection with the plates associated with mandibular distraction device, such attachment may be accomplished with screws that pass through the plates and into the bone to which attachment is desired, but any alternative attachment means that results in rigid connection between the bone and proximate side of the screw expansion mechanism will accomplish the desired result. For instance, pins or staples into the bone may also be possible, and adhesive bonding to the surface of the bone may be feasible.

While a maxillary-zygomatic-orbital distraction device is preferably bilateral and utilizes two screw expansion mechanisms as expansion means, additional expansion may be desirable in some cases, and only a unilateral device may be required where only distraction of only one side is desired. Additionally, different positioning of the expansion and second transmitting means such as plates, and different plate lengths and shapes may be utilized depending on the site where distraction is desired.

The device would be useful for achieving bone growth along a LeFort I osteotomy. Accordingly, the device is inserted under general anesthesia and anchored to the maxillary teeth and appropriate bone in substantially the same manner as the mandibular distraction device described above. A LeFort I osteotomy is also made and the expansion mechanisms are periodically actuated to permit osteogenesis. As noted above, the plates can be longer to permit their attachment to the temporal bones and LeFort II and or LeFort III osteotomies performed to obtain movement of the mid-face and maxilla with osteogenesis at the LeFort II and LeFort III sites.

When maxillary deficiency is corrected, the device can be removed or portions left implanted as osseous implants that can be utilized again if further distraction is necessary.

C. Buried Cranial Distraction Device

A variety of cranial and orbital zygomatic deformities exist, including but not limited to: (1) deformational head deformities, (2) torticollis with deformational head deformities, (3) craniofacial microsomia, and (4) syndromic and non-syndromic craniosynostosis. In the more common deformities, the patient presents with an asymmetric head shape because of torquing of the cranial base. Generally, the occipital area on one side is flattened, and there may be contralateral bulging of the forehead with anterior plagiocephaly. In essence, the entire cranial base is shifted, giving the head a parallelogram shape. The buried cranial distraction device embodiment of the present invention is useful in treatment of these deformities.

The internal or buried cranial distraction device of the present invention utilized a screw expansion mechanism as an expansion means attached on each side to the first transmitting means and the second transmitting means that take the form of plates that are fixed in place with screws. The device has a low profile so that it hugs the bone site where it is installed and may be entirely buried under the overlying soft tissue. Alternatively, only the plates may be buried and the expansion means is external to the subject, such as when wires penetrate the soft tissue overlying the bone to which plates are attached so that expansion mechanism lies near but outside of such tissue. Where device is entirely buried, a small chimney can be formed penetrating the soft tissue immediately above the actuation holes in the screw to allow insertion of an appropriately shaped activator to turn the screw in expansion means. This chimney may, for instance, be lined with a tube or sleeve of an appropriate material such as a stainless steel tube or Dacron, Gortex or other synthetic fabric. It may be covered with a silicon rubber cap or an appropriately formed cover or flap of Dacron, Gortex or other synthetic fabric or sheet material. Multiple devices may be placed across the open cranial sutures or when osteotomies are used across the zygoma or zygomatic-orbital complex if the cheekbone and zygomatic orbital region need anterior repositioning. The geometry of the plates may be appropriately configured and dimensioned in a variety of shapes and sized depending on the skull abnormality present and anchorage needed.

The buried cranial distraction device is placed across cranial sutures or across osteotomy lines (for example, orbital and zygomatic) to permit distraction osteogenesis. By applying the device across the open lambdoid suture, for instance, and gradually distracting the suture by actuation of the expansion mechanism, new bone is laid in between and the cranial base is gradually repositioned. Multiple devices may be necessary. For instance, one device may be placed across the lambdoid suture, while a second device is placed across the coronal suture or perhaps on the zygomatic body and arch.

The current treatment of choice for children with severe recession of the orbit and forehead secondary to a deformation and not a fused suture is surgery if the severity of the deformity warrants it. Thus, by placement of buried distraction devices that can be engaged through small openings in the scalp, the substantial trauma of a combined neurosurgical and craniofacial surgical procedure is avoided. In addition, more precise manipulation of the cranial base structures, the orbit and forehead and the cheek bone, as well as the occiput, will occur.

D. Intraorbital Expanding Devices

Patients with microphthalmus or anophthalmia and patients following enucleation of the globe for a variety of reasons such as trauma, tumors, infection, etc. may require repeated intraorbital prosthesis to prevent cessation of intraorbital growth as the patient ages. A variety of congenital abnormalities and/or conditions present during childhood necessitate placement of a variety of orbital prostheses. Ultimately, the orbital cavity is enlarged to a near symmetric size with a contralateral normal orbit and/or is both orbits are involved to a predetermined adult size. Following this, the permanent orbital prosthesis can then be placed. In some cases of microphthalmus or anophthalmia, an orbit itself is made with bone grafting and/or bone grafting in combination with orbital osteotomies for expansion. In these cases serial prostheses must also be used to prevent contraction of intraorbital volume. Ultimately, a permanent prosthesis is placed. During serial placement of orbital prostheses, retention of the prosthesis can be a problem. This may lead to repeated extrusion of the orbital prosthesis.

Additional embodiments of the present invention are intraorbital expanding devices. Each of the intraorbital expanding devices are essentially hemispherically shaped bodies segmented into multiple segments, preferably between about two and about six segments, more preferably between about two and about four segments and most preferably two or three segments. The segments can be solid or hollow. As will be appreciated by those skilled in the art, the segments may be formed of any material having appropriate mechanical characteristics and demonstrated biocompatibility. The devices are placed surgically after appropriate impressions of the eye socket have been take and the device fabricated to fit the patient's eye socket.

A screw expansion mechanism is used as an expansion means and attaches segments to be forced apart by rotation of the expansion means, which preferably comprises a screw.

Segments are attached by a two-way screw expansion mechanism that has two screws that are oriented and operate at right angles to each other. Thus, expansion mechanism is fixed to segment and movably attached to segments so that rotation of screw causes segment to move relative to segment along the axis of screw, and rotation of screw causes segment to move along the axis of screw, which is perpendicular to the direction of movement of segment. Such two-way screw expansion mechanisms, called "multidimensional expansion screws" also may be obtained from one or more of the sources for expansion screws identified above. An expansion mechanism that may be superior to mechanism in the device would move segment along a direction separated 120° from the direction of movement of segment.

The intraorbital expander devices may be fixed in the patient's orbit by a variety of means. For instance screws may be passed through the segments and into the bone against which those segments rest. Alternatively, projections from the segments can lodge in the intraorbital bone as the devices are expanded, staples can extend from the segments to impale adjacent bone as the device opens, plates can connect the segments to adjacent bone, or the segments can be covered with a resilient material such as silicone rubber to lock the device in place as the segments are separated. As will also be appreciated by reference to the anatomy of the human orbit, if the segments are provided with an appropriate recess in which the orbital margin seats, the devices will lock themselves in position as they are expanded where the patient presents with orbital geometry that is normal or similar to normal in this respect.

Use of the intraorbital expanding device of the present invention permits continual expansion without the need for removal and serial placement of new prostheses. Furthermore, the devices include structures or geometry for retention that prevent extrusion. As explained above, such structures include either acrylic projections that lodge in the intraorbital bone and/or into notches or drill holes made by the inserting surgeon, and/or by metallic stapling devices pinned against and into the orbital bone.

E. Intraorbital, Buccal Tissue Expanding Device

Patients with vestibular tissue deficiency secondary to burns, trauma, tumor resection, mandibular atrophy secondary to loss of teeth, and a variety of other causes often require vestibuloplasty. This may be limited to the anterior region or the posterior vestibule. This may be related both to the mandibular, lower buccal sulcus, and the maxillary upper buccal sulcus. Patients with congenital deformities such as cleft lip and palate and other craniofacial deformities may also have tissue deficiencies in these areas. Current treatment involves a vestibuloplasty by releasing the scarred and contracted vestibular tissue and bringing in new tissue either by means of rotation flaps or tissue grafting or free tissue transfer. Following correction of vestibular tissue deficiencies, and intraoral stent is usually manufactured and placed. Often this is fixated to the teeth by means of stainless steel clasps and occasionally a variety of other fixation devices, usually circa mandibular and/or maxillary suspension wires. The stent itself is typically left in for prolonged periods in order to prevent contraction of the newly introduced tissue and recurrence of the original problem. Such devices are either not adjustable or are not easily adjusted.

Another embodiment of the present invention is an intraoral, buccal tissue expanding device. Such a device may be used following vestibuloplasty, grafting, free tissue transfer, as a preliminary expanding device, or as the sole means of tissue expansion. The details of the appropriate structure for buccal tissue expanding device will, as is the case with the other embodiments of the present invention described above, depend on the particular needs of the patient for whom the device is made.

Exemplary mandibular device is bilaterally symmetrical and therefore will be described primarily by reference to one side, in this case the right side. A tooth stent forms the first transmitting means is bonded to the mandibular teeth and is connected through a triple-acting expansion mechanism forming the expansion means to a posterior tissue expanding stent and an anterior tissue expanding plate that serve as the second transmitting means. A curved buccal tissue expanding stent is attached to the anterior expanding plate or stent. The device is attached to the teeth by bonding or cementing the tooth stent to the mandibular teeth so that the stents press against the new vestibular tissue.

Rotation of screw in expansion mechanism causes lateral movement of posterior and anterior tissue expanding stents to permit exertion of desired pressure on adjacent tissue. Rotation of double-acting screw in expansion mechanism causes posterior movement of posterior tissue expanding stent and anterior movement of both anterior tissue expanding stent and buccal tissue expanding stent. Such adjustment of the positions of stents results in active tissue expansion to prevent contraction of newly introduced vestibular tissues.

EXAMPLES

Example I

Biodegradable Distraction Device for use in Mandibular Distraction, LeFort III Distraction, Le Forte I Distraction or Monobloc Distraction Methods As depicted in FIGS. 1-6, the present invention can be used in a wide variety of distraction surgical methods and procedures. Although some of the components of the device in FIGS. 1-6, are represented as metal or other non-biodegradable, bioerodible or bioresorbable materials, biodegradable, bioerodible or bioresorbable materials can be used for any of these components. Preferably, the activating means 22 is not made of such biodegradable, bioerodible or bioresorbable materials, but that need not be the case. The activating device 22 is depicted without a turn-key, which when turned one rotation clockwise results in a distraction of about 0.5 mm.

A variety of surgical procedures may employ the internal biodegradable distraction device of the present invention including for example monobloc distraction with and without facial bipartition and other osteotomies, LeFort III distraction with or without subcranial facial bipartition, LeFort II, LeFort I, zygomatic and mandibular distraction. Since the system is biodegradable additional substantial surgical procedures will not be required to remove the implanted device. The following is a general description of a distraction procedure using one aspect of a distraction device of the present invention.

A bioerodible polymer mesh (Maropore, Inc. San Diego, Calif.) is utilized to secure the device to bone. The mesh is attached to either side of the metallic screw of the expansion mechanism by bioerodible slots that retain the footplate of the metallic screw. The bioerodible slots in turn are attached to the mesh with biodegradable screws. The mesh is heat malleable, consequently it may be cut and contoured to fit virtually any anatomical site. Standard osteotomies are performed. The osteonomy is spanned with the distractor that is attached to the bone with biodegradable mesh and screws. Test distraction is performed to determine the total distraction distance and to ensure that there is no evidence of detachment of the biodegradable mesh and screws. Test distraction also enables the surgeon to determine if the osteotomy is complete and the bone segment to be transported is fully mobilized.

Distraction is initiated on post-operative days 5-7 and carried out at approximately 1.0 mm per day divided into two sessions per day. Preoperative radiologic and clinical findings dictate the extent of distraction. Intraoperative test distraction also enables the surgeon to determine the extent of distraction that will be necessary for correction of the particular deformity. Careful postoperative follow-up enables the surgeon to determine when distraction is complete. Unlike the large exposure that is necessary to remove metallic screws, the biodegradable device permits easier removal if necessary. The metallic distraction screw that is activated and driven by an external cable sheathed in TEFLON is turned counter-clockwise. The footplates of the distraction screw slide out of the biodegradable slots. The mesh does not require removal and usually degrades within about 18 to 36 months after implantation. Once distraction is complete the metallic distraction screw is rotated clockwise until it is disengaged from the distraction footplate and removed from the patient. Under direct or endoscopic exposure, a new bioerodible stabilizer is placed into the anterior biodegradable slot of the attachment part which is attached to the biodegradable mesh or plate and screwed into the posterior bone segment. This permits earlier removal of the device and rigid stabilization of the osteotomies and distraction callus, permitting bony consolidation. All wounds are closed under standard medical procedures.

FIG. 4 depicts as region of a skull that has undergone an osteotomy to fully free a portion of the "cheek bone." This freed region is the region to be distracted during the procedure. As shown in FIG. 1 depicts two portions of a transmitting means includes a macroporous sheet 32 of PLA/PGA and a flange-engaging structure 34 suitable for engaging a flange of an expansion means 12. In this aspect of the present invention the first transmitting means 10A and the second transmitting means 10B have substantially similar structures. The particular structures of the flange-engaging structure 34 is provided in FIGS. 6A-6C. As shown in FIG. 1 the flange-engaging structure 34 can be engaged to the macroporous sheet 32 using appropriate attaching devices 36, in this case bioresorbable PLA/PGA screws.

Two transmitting means 10 of FIG. 1 can be engaged with engaged with an expansion means 12 that includes flanges that engage the flange-engaging structures 34 of the transmitting means (FIGS. 2-3). In this figure, the expansion means 12 is depicted as being made of non-biodegradable, non-bioerodible or non-bioresorbable materials, but that need not be the case because the expansion means can be made of such biodegradable, bioerodible or bioresorbable materials in whole or in part. As shown in FIG. 3, the nature of the engagement of the transmitting means and the expansion means as reversible. In the pictured aspect of the present invention, this reversible engagement is exhibited for both the first transmitting means and the second transmitting means. Thus, after distraction is accomplished, the expansion means can be disengaged from the remainder of the distraction device and removed. It is relatively simple to remove the expansion means from a subject as opposed to the transmitting means. Thus, there is a reduced amount of cumulative trauma that the subject is exposed to. The proximal transmitting means: expansion means: distal transmitting means has been trimmed and configured for use on the osteotomy depicted in FIG. 4. Note that the proximal transmitting means has been altered from its planar configuration.

The transmitting means has a heat malleable nature, and a transmitting means is contacted with water hot enough to induce malleability of the material and the shape of the material is changed to conform to the shape of the region to which it will be attached. As shown in FIG. 4, the distraction device is depicted in place at the site of osteotomy prior to distraction. The distraction device includes heat-malleable materials that have been molded to the contours of the attachment points of the distraction device. The transmitting means 10 are secured to the skull using PLA/PGA screws in holes drilled into the bone. During a distraction procedure, the implementation of the distraction device would be complete. Distraction would be accomplished by engaging the expansion means 12 with an activation means 22 to gradually increase the distraction distance.

FIG. 5 depicts the distraction device after distraction has taken place. This figure depicts a mock-up skull, thus the distraction space has not been filled with distraction tissue. At this point in the procedure, the expansion means 12 would be removed by disengaging the expansion means 12 from the transmitting means 10, such as by engaging the activation means 22 to decrease the length of the expansion device. The expansion means can be removed using surgical procedures, preferably endoscopic procedures. If the expansion means is made in whole or in part of biodegradable, bioerodible or bioresorbable materials, then the expansion means can optionally be removed.

Figure 9:
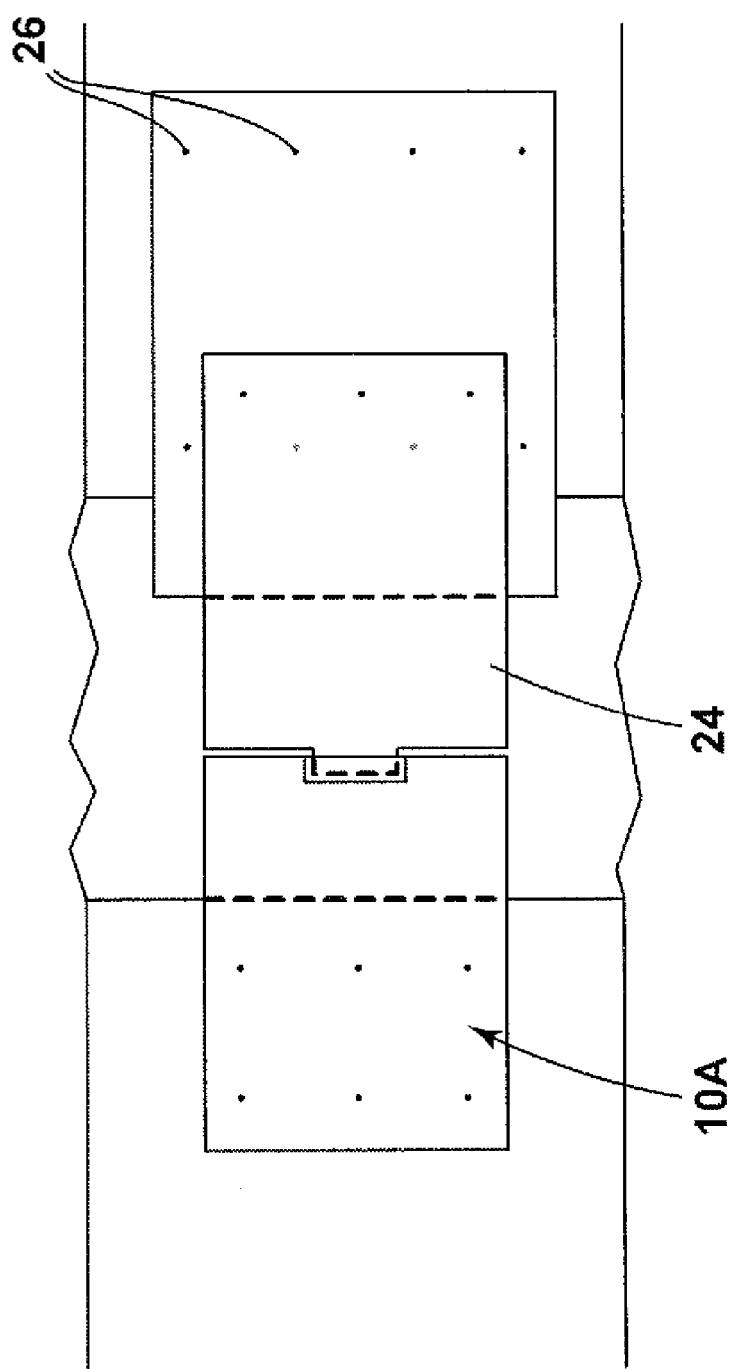
FIG. 9 is a conceptual diagram depicting the use of stabilizing means in a distraction procedure.

Optionally, at least one stabilizer 24, 28 can be inserted into, over or around the expansion space and appropriately secured such that the distracted tissue is mechanically stabilized (FIG. 7 or FIG. 9). Such stabilizer(s) are preferably made at least in part of biodegradable, bioerodible or bioresorbable material, such as PLA/PGA, preferably macroporous PLA/PGA. In one aspect of the present invention, the stabilizing means can engage structures on the transmitting means 10A (FIG. 9). In one aspect of the present invention, the stabilizing means of FIG. 7 and FIG. 9 can be combined. In addition, guiding means 20 can be used during distraction or after distraction to guide or stabilize the distraction device (FIG. 8). The guiding means is preferably made in whole or in part of a biodegradable, bioerodible or bioresorbable material. As shown in FIG. 8, as preferred aspect of the present invention is a guiding means that engages both the first and second transmitting means, but that is not a requirement of the present invention. For example, the guiding means can be attached to a tissue structure in proximity to the distraction site, such as bone.

In one aspect of the present invention alternative structures of FIG. 10 depict a unidirectional distraction device that includes engaging structures 18 such as those in "shark's tooth" configurations and mating structures 16 to match the engaging structures such as indentations or holes (such as those in macroporous structures) to allow substantially unidirectional sliding of the transmitting means and can act to stabilize the distraction device. Preferably, the engaging structures and/or the mating structures are made in whole or in part of biodegradable, bioerodible or bioresorbable materials.

The engaging structures and mating structures can be provided on any appropriate surface on a distraction device that come in contact or in close proximity to each other. For example, the first and second transmitting means can be designed to overlap each other during at least a portion of a distraction procedure. Alternatively, the expansion means can overlap with one or both of the first or second transmitting means during at least a portion of a distraction procedure.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A connective tissue distraction device comprising:
   first transmitting means for transmitting force to a first tissue region, and including a first flange engagement structure;
   second transmitting means for transmitting force to a second tissue region, and including a second flange engagement structure; and
   an expansion means, including a screw expansion mechanism having a proximal end and a distal end, the proximal end including a first L-shaped flange defined by a first vertical plate that receives the screw expansion mechanism and a first horizontal plate extending from the first vertical plate to engage the first flange engagement structure of the first transmitting means, the first flange engagement structure sized to receive the first horizontal plate, the distal end including a second L-shaped flange defined by a second vertical plate connected to the distal end of the screw expansion mechanism and a second horizontal plate extending from the second vertical plate to engage the second flange engagement structure of the second transmitting means, the second flange engagement structure sized to receive the second horizontal plate,
   the expansion means for exerting force distracting the first transmitting means from the second transmitting means to create a distraction space for formation of distracted connective tissue,
   wherein the first L-shaped flange disengages from the first flange engagement structure and the L-shaped second flange disengages from the second flange engagement structure,
   wherein at least one of the first transmitting means, the second transmitting means and the expansion means comprises a biodegradable, bioerodible or bioresorbable material.

2. The connective tissue distraction device of claim 1, wherein the first transmitting means comprises a structure for attachment to bone.

3. The connective tissue distraction device of claim 2, wherein the structure for attachment to bone comprises at least in part a biodegradable, bioerodible or bioresorbable material.

4. The connective tissue distraction device of claim 2, wherein the structure for attachment to bone is a plate.

5. The connective tissue distraction device of claim 2, wherein the structure for attachment to bone is attached to bone via at least one screw.

6. The connective tissue distraction device of claim 5, wherein the screw is at least in part biodegradable, bioerodible or bioresorbable material.

7. The connective tissue distraction device of claim 1, wherein the second transmitting means comprises a structure for attachment to bone.

8. The connective tissue distraction device of claim 7, wherein the structure for attachment to bone is at least in part a biodegradable, bioerodible or bioresorbable material.

9. The connective tissue distraction device of claim 7, wherein the structure for attachment to bone is a plate.

10. The connective tissue distraction device of claim 7, wherein the structure for attachment to bone is attached to bone via at least one screw.

11. The connective tissue distraction device of claim 10, wherein the screw is at least in part a biodegradable, bioerodible or bioresorbable material.

12. The connective tissue distraction device of claim 1, wherein at least one of the first transmitting means, second transmitting means or the expansion means comprise a malleable or heat malleable material.

13. The connective tissue distraction device of claim 1, wherein the first tissue region comprises connective tissue.

14. The connective tissue distraction device of claim 1, wherein the first tissue region comprises bone.

15. The connective tissue distraction device of claim 1, wherein the second tissue region comprises connective tissue.

16. The connective tissue distraction device of claim 1, wherein the second tissue region comprises bone.

17. The connective tissue distraction device of claim 1, further comprising an activation means.

18. The connective tissue distraction device of claim 17, wherein the activation means is directly or indirectly engaged with expansion means.

19. The connective tissue distraction device of claim 18, wherein the activation means is reversibly engaged with the expansion means.

20. The connective tissue distraction device of claim 17, wherein at least a portion of the activation means is external to the subject.

21. A connective tissue distraction device comprising:
    a first transmitting structure that transmits force to a first tissue region;
    a second transmitting structure that transmits force to a second tissue region; and
    an expansion structure that distracts the first transmitting structure from the second transmitting structure to create a distraction space for formation of distracted connective tissue, the expansion structure further comprising:
    a screw expansion mechanism;
    a proximal end having a first L-shaped flange defined by a first vertical plate that receives the screw expansion mechanism and a first horizontal plate extending from the first vertical plate to engage a first slot of the first transmitting structure, the first slot sized to receive the first horizontal plate; and
    a distal end having a second L-shaped flange defined by a second vertical plate connected to a distal end of the screw expansion mechanism and a second horizontal plate extending from the second vertical plate to engage a second slot of the second transmitting structure, the second slot sized to receive the second horizontal plate;
    wherein at least one of the first transmitting structure, the second transmitting structure and the expansion structure comprises a biodegradable, bioerodible or bioresorbable material.

22. The device of claim 21, wherein the first and second transmitting structures each comprise one of a plate, a stent, a mesh or an implant.

23. The device of claim 21, further including attachment structures that attach the first and second transmitting structures to the first and second tissues regions, respectively.

24. The device of claim 23, wherein the attachment structures comprise one of screws, staples, tacks, pins, or nails.

25. The device of claim 23, wherein the attachment structures comprise a biodegradable, bioerodible or bioresorbable material.

26. The device of claim 23, wherein the first and second tissue regions each comprise one of bone or connective tissue.

* * * * *